(12) United States Patent
Tanaka et al.

(10) Patent No.: US 9,234,200 B2
(45) Date of Patent: Jan. 12, 2016

(54) OLIGONUCLEOTIDE, GLUCOCORTICOID SENSITIVITY ENHANCER, PHARMACEUTICAL COMPOSITION, AND EXPRESSION VECTOR

(71) Applicant: National University Corporation Tokyo University of Agriculture and Technology, Tokyo (JP)

(72) Inventors: Akane Tanaka, Tokyo (JP); Hiroshi Matsuda, Tokyo (JP); Akira Matsuda, Tokyo (JP)

(73) Assignee: NATIONAL UNIVERSITY OF CORPORATION TOKYO UNIVERSITY OF AGRICULTURE AND TECHNOLOGY, Tokyo (JP)

( * ) Notice: Subject to any disclaimer, the term of this patent is extended or adjusted under 35 U.S.C. 154(b) by 0 days.

(21) Appl. No.: 14/365,092

(22) PCT Filed: Oct. 31, 2012

(86) PCT No.: PCT/JP2012/078245
§ 371 (c)(1),
(2) Date: Jun. 12, 2014

(87) PCT Pub. No.: WO2013/088853
PCT Pub. Date: Jun. 20, 2013

(65) Prior Publication Data
US 2015/0118744 A1    Apr. 30, 2015

(30) Foreign Application Priority Data

Dec. 15, 2011 (JP) ................................. 2011-274897

(51) Int. Cl.
*C12N 15/113* (2010.01)
*A61K 31/7088* (2006.01)
*C12N 15/115* (2010.01)

(52) U.S. Cl.
CPC ........ *C12N 15/1138* (2013.01); *A61K 31/7088* (2013.01); *C12N 15/113* (2013.01); *C12N 15/115* (2013.01); *C12N 2310/13* (2013.01); *C12N 2310/16* (2013.01); *C12N 2320/33* (2013.01)

(58) Field of Classification Search
None
See application file for complete search history.

(56) References Cited

U.S. PATENT DOCUMENTS

| 5,624,803 | A  | * | 4/1997 | Noonberg et al. ........... 435/6.16 |
| 2005/0164271 | A1 | * | 7/2005 | Bhanot et al. .................... 435/6 |
| 2007/0135367 | A1 |   | 6/2007 | Hagiwara et al. |
| 2010/0016359 | A1 |   | 1/2010 | Hagiwara et al. |
| 2013/0079369 | A1 |   | 3/2013 | Hagiwara et al. |

FOREIGN PATENT DOCUMENTS

WO    2005/063293 A1    7/2005

OTHER PUBLICATIONS

Karakama, et al., "Inhibition of Hepatitis C Virus Replication by a Specific Inhibitor of Serine-Arginine-Rich Protein Kinase," *Antimicrob. Agents Chemother.*, vol. 54(8), pp. 3179-3186 (2010).
Matsuda, et al., "A novel NF-KB inhibitor improves glucocorticoid sensitivity of canine neoplastic lymphoid cells by up-regulating expression of glucocorticoid receptors," *Res. Vet. Sci.*, vol. 89(3), pp. 378-382 (2010).
Matsuda, et al., The 14th International Congress of Immunology, Presentation No. WS/PP-089-06, Aug. 24, 2010.
Paradis, et al., "hnRNP I/PTB can antagonize the splicing repressor activity of SRp30c," *RNA*, vol. 13, pp. 1287-1300 (2007).
Piotrowska, et al., "Glucocorticoid Receptor α and β Variant Expression Is Associated with ASF/SF2 Splicing Factor Upregulation in HT-29 Colon Cancer and MCF-7 Breast Carcinoma Cells," *Arch. Med. Res.*, vol. 40, pp. 156-162. (2009).
Wang, et al., "Tau Exons 2 and 10, Which Are Misregulated in Neurodegenerative Diseases, Are Partly Regulated by Silencers Which Bind a SRp30c•SRp55 Complex That Either Recruits or Antagonizes htra2β1," *J Biol Chem.*, vol. 280, No. 14, pp. 14230-14239 (2005).
Watanuki, et al., "Increased expression of splicing factor SRp20 mRNA in bipolar disorder patients," *J. Affect. Disord.*, vol. 110(1-2), pp. 62-69 (2008).
Xu, et al., "Serine-Arginine-rich Protein p30 Directs Alternative Splicing of Glucocorticoid Receptor Pre-mRNA to Glucocorticoid Receptor β in Neutrophils," *J. Biol. Chem.*, vol. 278, pp. 27112-27118 (2003).

* cited by examiner

*Primary Examiner* — Tracy Vivlemore

(57) ABSTRACT

An oligonucleotide that inhibits the binding of a serine/arginine-rich protein 30c (SRp30c) to a pre-mRNA of a glucocorticoid receptor gene in vivo.

14 Claims, 6 Drawing Sheets

```
                         SEQUENCE LISTING

<160> NUMBER OF SEQ ID NOS: 22

<210> SEQ ID NO 1
<211> LENGTH: 31
<212> TYPE: DNA
<213> ORGANISM: Artificial Sequence
<220> FEATURE:
<223> OTHER INFORMATION: Oligonucleotide 1

<400> SEQUENCE: 1
ctttctggtt ttaaccacat aacattctat a                              31

<210> SEQ ID NO 2
<211> LENGTH: 34
<212> TYPE: DNA
<213> ORGANISM: Artificial Sequence
<220> FEATURE:
<223> OTHER INFORMATION: Oligonucleotide 2

<400> SEQUENCE: 2
aaaagggcac agcttctttt cccatttaat gaaa                           34

<210> SEQ ID NO 3
<211> LENGTH: 31
<212> TYPE: DNA
<213> ORGANISM: Artificial Sequence
<220> FEATURE:
<223> OTHER INFORMATION: Oligonucleotide 3

<400> SEQUENCE: 3
taagatgact ttcttttccc ccacgtatcc t                              31

<210> SEQ ID NO 4
<211> LENGTH: 23
<212> TYPE: DNA
<213> ORGANISM: Artificial Sequence
<220> FEATURE:
<223> OTHER INFORMATION: Oligonucleotide 4

<400> SEQUENCE: 4
```
tttgtcccca ttatatagca ttt                                                    23

<210> SEQ ID NO 5
<211> LENGTH: 21
<212> TYPE: DNA
<213> ORGANISM: Artificial Sequence
<220> FEATURE:
<223> OTHER INFORMATION: Oligonucleotide 5

<400> SEQUENCE: 5
cagatttttt tattatgatg t                                                      21

<210> SEQ ID NO 6
<211> LENGTH: 22
<212> TYPE: DNA
<213> ORGANISM: Artificial Sequence
<220> FEATURE:
<223> OTHER INFORMATION: GRa-Fw

<400> SEQUENCE: 6
ctatgcatga agtggttgaa aa                                                     22

<210> SEQ ID NO 7
<211> LENGTH: 19
<212> TYPE: DNA
<213> ORGANISM: Artificial Sequence
<220> FEATURE:
<223> OTHER INFORMATION: GRa-Rv

<400> SEQUENCE: 7
tttcagctaa catctcggg                                                         19

<210> SEQ ID NO 8
<211> LENGTH: 20
<212> TYPE: DNA
<213> ORGANISM: Artificial Sequence
<220> FEATURE:
<223> OTHER INFORMATION: GRb-Fw

<400> SEQUENCE: 8
gaaggaaact ccagccagaa                                                        20

<210> SEQ ID NO 9
<211> LENGTH: 24
<212> TYPE: DNA
<213> ORGANISM: Artificial Sequence
<220> FEATURE:
<223> OTHER INFORMATION: GRb-Rv

<400> SEQUENCE: 9
ccacataaca ttttcatgca taga                                                   24

<210> SEQ ID NO 10
<211> LENGTH: 20
<212> TYPE: DNA
<213> ORGANISM: Artificial Sequence
<220> FEATURE:
<223> OTHER INFORMATION: GAPDH-Fw

<400> SEQUENCE: 10
atggccttcc gtgttcctac                                                        20

<210> SEQ ID NO 11
<211> LENGTH: 22
<212> TYPE: DNA
<213> ORGANISM: Artificial Sequence

```
<220> FEATURE:
<223> OTHER INFORMATION: GAPDH-Rv

<400> SEQUENCE: 11
tgatgtcatc atacttggca gg                                            22

<210> SEQ ID NO 12
<211> LENGTH: 20
<212> TYPE: DNA
<213> ORGANISM: Artificial Sequence
<220> FEATURE:
<223> OTHER INFORMATION: ERa-Fw

<400> SEQUENCE: 12
cctactacct ggagaacgag                                               20

<210> SEQ ID NO 13
<211> LENGTH: 20
<212> TYPE: DNA
<213> ORGANISM: Artificial Sequence
<220> FEATURE:
<223> OTHER INFORMATION: ERa-Rv

<400> SEQUENCE: 13
ctcttcggtc ttttcgtatg                                               20

<210> SEQ ID NO 14
<211> LENGTH: 20
<212> TYPE: DNA
<213> ORGANISM: Artificial Sequence
<220> FEATURE:
<223> OTHER INFORMATION: ERb-Fw

<400> SEQUENCE: 14
aaaagaatca ttcaatgaca                                               20

<210> SEQ ID NO 15
<211> LENGTH: 20
<212> TYPE: DNA
<213> ORGANISM: Artificial Sequence
<220> FEATURE:
<223> OTHER INFORMATION: ERb-Rv

<400> SEQUENCE: 15
attaacacct ccatccaaca                                               20

<210> SEQ ID NO 16
<211> LENGTH: 33
<212> TYPE: DNA
<213> ORGANISM: Artificial Sequence
<220> FEATURE:
<223> OTHER INFORMATION: ON4-Sense

<400> SEQUENCE: 16
gatccatttg tccccattat atagcatttt ttg                                33

<210> SEQ ID NO 17
<211> LENGTH: 33
<212> TYPE: DNA
<213> ORGANISM: Artificial Sequence
<220> FEATURE:
<223> OTHER INFORMATION: ON4-Antisense

<400> SEQUENCE: 17
aattcaaaaa atgctatata tgggggacaa atg                                33
```

-continued

<210> SEQ ID NO 18
<211> LENGTH: 24
<212> TYPE: DNA
<213> ORGANISM: Artificial Sequence
<220> FEATURE:
<223> OTHER INFORMATION: ON4-Fw

<400> SEQUENCE: 18
atggactatc atatgcttac cgta                                           24

<210> SEQ ID NO 19
<211> LENGTH: 20
<212> TYPE: DNA
<213> ORGANISM: Artificial Sequence
<220> FEATURE:
<223> OTHER INFORMATION: ON4-Rv

<400> SEQUENCE: 19
taatgacccc gtaattgatt                                                20

<210> SEQ ID NO 20
<211> LENGTH: 24
<212> TYPE: DNA
<213> ORGANISM: Artificial Sequence
<220> FEATURE:
<223> OTHER INFORMATION: Pre-mRNA-Fw

<400> SEQUENCE: 20
gagggaagga aactccagcc agaa                                           24

<210> SEQ ID NO 21
<211> LENGTH: 20
<212> TYPE: DNA
<213> ORGANISM: Artificial Sequence
<220> FEATURE:
<223> OTHER INFORMATION: Pre-mRNA-Rv

<400> SEQUENCE: 21
tttcagctaa catctcgggg                                                20

<210> SEQ ID NO 22
<211> LENGTH: 1492
<212> TYPE: DNA
<213> ORGANISM: Homo sapiens
<220> FEATURE:
<223> OTHER INFORMATION: GR156091-157582

<400> SEQUENCE: 22
ttcctttata gaatgttatg tggttaaaac cagaaagcac atctcacaca ttaatctgat     60
tttcatccca acaatcttgg cgctcaaaaa atagaactca atgagaaaaa gaagattatg    120
tgcacttcgt tgtcaataat aagtcaactg atgctcatcg acaactatag gaggcttttc    180
attaaatggg aaaagaagct gtgccctttt aggatacgtg ggggaaaaga aagtcatctt    240
aattatgttt aattgtggat ttaagtgcta tatggtggtg ctgtttgaaa gcagatttat    300
ttcctatgta tgtgttatct ggccatccca acccaaactg ttgaagtttg tagtaacttc    360
agtgagagtt ggttactcac aacaaatcct gaaaagtatt tttagtgttt gtaggtattc    420
tgtgggatac tatacaagca gaactgaggc acttaggaca taacactttt ggggtatata    480
tatccaaatg cctaaaacta tgggaggaaa ccttggccac cccaaaagga aaactaacat    540
gatttgtgtc tatgaagtgc tggataatta gcatgggatg agctctgggc atgccatgaa    600
ggaaagccac gctcccttca gaattcagag gcagggagca attccagttt cacctaagtc    660

```
tcataatttt agttcccttt taaaaaccct gaaaactaca tcaccatgga atgaaaaata      720
ttgttataca atacattgat ctgtcaaact tccagaacca tggtagcctt cagtgagatt      780
tccatcttgg ctggtcactc cctgactgta gctgtaggtg aatgtgtttt tgtgtgtgtg      840
tgtctggttt tagtgtcaga agggaaataa aagtgtaagg aggacacttt aaaccctttg      900
ggtggagttt cgtaatttcc cagactattt tcaagcaacc tggtccaccc aggattagtg      960
accaggtttt caggaaagga tttgcttctc tctagaaaat gtctgaaagg attttatttt     1020
ctgatgaaag gctgtatgaa aatacccctcc tcaaataact tgcttaacta catatagatt    1080
caagtgtgtc aatattctat tttgtatatt aaatgctata taatgggggac aaatctatat    1140 tatactgtgt atggcattat taagaagctt tttcattatt ttttatcaca gtaattttaa     1200
aatgtgtaaa aattaaaacc agtgactcct gtttaaaaat aaaagttgta gttttttatt     1260
catgctgaat aataatctgt agttaaaaaa aaagtgtctt tttacctacg cagtgaaatg     1320
tcagactgta aaaccttgtg tggaaatgtt taacttttat tttttcattt aaatttgctg     1380
ttctggtatt accaaaccac acatttgtac cgaattggca gtaaatgtta gccatttaca     1440
gcaatgccaa atatggagaa acatcataat aaaaaaatct gcttttcat ta              1492
```

OLIGONUCLEOTIDE, GLUCOCORTICOID SENSITIVITY ENHANCER, PHARMACEUTICAL COMPOSITION, AND EXPRESSION VECTOR

CROSS-REFERENCE TO RELATED APPLICATIONS

This application is the U.S. National Stage entry of PCT/JP2012/078245, filed Oct. 31, 2012, which claims benefit of Japanese Patent Application No. 2011-274897, filed Dec. 15, 2011, the disclosures of each are herein incorporated by reference.

TECHNICAL FIELD

This present invention relates to an oligonucleotide, a glucocorticoid sensitivity enhancer, a pharmaceutical composition, and an expression vector.

BACKGROUND ART

Glucocorticoids are a class of hormones produced by the adrenal cortex and involved in metabolism and immunity. Since glucocorticoids have strong anti-inflammatory effects and immunosuppressive effects, artificially synthesized glucocorticoids have been used as drugs for treating allergic diseases and autoimmune diseases.

Furthermore, since glucocorticoids have growth inhibitory effects on lymphocytes that have become cancerous, artificially synthesized glucocorticoids have been used in chemotherapy for lymphoma or lymphocytic leukemia. Since it is quite rare for the administration of glucocorticoids to produce side effects such as myelosuppression or severe gastrointestinal symptoms, glucocorticoids are essential drugs for treating lymphoma or lymphocytic leukemia.

Glucocorticoids have been used for the treatment of various diseases. However, there are cases in which some patients exhibit resistance to glucocorticoids, and glucocorticoids do not exert effects in such cases. It is reported that from 5% to 10% of the patients with asthma, about 30% of the patients with rheumatic diseases, from 20% to 50% of the patients with inflammatory bowel diseases, and from 10% to 25% of the patients with childhood acute lymphocytic leukemia have resistance to glucocorticoids. Therefore, development of a technique for canceling resistance to glucocorticoids has been requested.

The following findings have been reported with regard to glucocorticoid receptors (GRs).

GRs, when bound to glucocorticoids, function as transcription factors in nuclei. The base sequence of a human GR gene is known (NR3C1, Gene ID: 2908, NCBI Reference Sequence: NC_000005.9). Nine exons are present in the human GR gene, and two splicing variants, GRα and GRβ, are generated by alternative splicing within exon 9 (having 4,111 bases).

GRα is a protein having 777 amino acid residues translated from a mature mRNA formed by joining together of exons 1 to 9. GRα translocates into the nucleus in a ligand-dependent manner and functions as a transcription factor.

GRβ is a protein having 742 amino acid residues translated from a mature mRNA formed by joining together of exons 1 to 8 and a part of exon 9 (from 2631st base to 4111th base from the 5'-end of exon 9). GRβ lacks a part of the ligand-binding domain, and has no ligand-binding capacity. In the nucleus, GRβ competitively antagonizes GRα to which a ligand is bound, and inhibits the transcription factor activity of GRα.

With regard to glucocorticoid resistance of cells, the following reports have been made.

It has been reported that, in cell lines (CL-1 cells, GL-1 cells) derived from canine lymphoma or leukemia, glucocorticoid resistance is canceled by inhibiting the function of nuclear factor-κB (NF-κB), and cell proliferation is inhibited by the addition of a glucocorticoid (for example, see Document 1). This suggests that the inhibition of NF-κB function increases GR expression levels in the cells, thereby making it easier for the cell proliferation inhibitory effects of glucocorticoids to be exerted on the cells.

It has also been reported that, in Raji cells derived from human Burkitt's lymphoma and peripheral blood-derived cells from patients with acute lymphocytic leukemia, glucocorticoid resistance is canceled, and GRα expression levels are increased, by inhibiting NF-κB function using an siRNA (for example, see Document 2). This result suggests the possibility that glucocorticoid resistance is canceled by increased expression of GRα in the cells.

With regard to GR expression, the following reports have been made.

It has been reported that, in a colon cancer cell line (HT-29 cells) and a breast cancer cell line (MCF-7 cells), histone deacetylase inhibitors such as trichostatin A and sodium butyrate and a DNA methyltransferase inhibitor 5-aza-2'-deoxycytidine increase GRα expression levels while decreasing GRβ expression levels (for example, see Document 3). At the same time, the expression level of ASF/SF2, which is a type of serine/arginine rich protein (SR protein), increases, suggesting the possibility that ASF/SF2 may be involved in the regulation of the splicing of the GR mRNAs. SR proteins are splicing factors, and regulate the splicing of pre-mRNAs into mature mRNAs in the nucleus.

It has been reported that a study comparing mRNA levels in peripheral lymphocytes from 28 healthy volunteers reveals the negative correlation between the expression level of serine/arginine-rich protein 30c (SRp30c), which is a type of SR protein, and the ratio of the GRα expression level to the GRβ expression level (GRα/GRβ) (for example, see Document 4).

It has also been reported that, in a neutrophil-like cell line (retinoic acid-stimulated PLB-985 cells), knocking-down of SRp30c using antisense oligonucleotides results in a decrease in the expression levels of the GRβ mRNA and an increase in the expression levels of the GRα mRNA (for example, see Document 5).

In addition, it was found that a 5-base sequence of AGGAC is present in the GR gene at relatively high frequency, and this sequence is expected to be an SRp30c recognition sequence (for example, see Document 6).

These findings suggest that the alternative splicing within exon 9 of the GR gene is regulated by SRp30c, which is a type of SR protein. That is, the above findings suggest that a site to which SRp30c binds is present in exon 9 of the pre-mRNA of GR, and that SRp30c binds to this site and regulates the splicing of the pre-mRNA of GR into the mature mRNA of GRβ.

However, there are no reports about whether or not the glucocorticoid sensitivity of cells is actually altered by inhibiting SRp30c function, and this point is unclear.

Meanwhile, a technique for inhibiting a function of an SR protein by inhibiting the phosphorylation of the SR protein is disclosed. For example, a technique is disclosed (for example, see Documents 7 and 8) in which an isonicotinamide compound SRPIN 340, which is an inhibitor of an SR protein kinase, is used as an antiviral agent.

Document 1: Matsuda A, et al. Res. Vet. Sci., 2010, 89(3): 378-382.

Document 2: Matsuda A, et al. The 14th International Congress of Immunology, August 2010, Volume 22, Supplement number 1, p. v8.

Document 3: Piotrowska H, et al. Arch. Med. Res., 2009, 40: 156-162.

Document 4: Watanuki T, et al. J. Affect. Disord., 2008, 110(1-2): 62-69.

Document 5: Xu Q, et al. J. Biol. Chem., 2003, 278: 27112-27118.

Document 6: Paradis C, et al. RNA, 2007, 13: 1287-1300.

Document 7: Karakama Y, et al. Antimicrob. Agents Chemother., 2010, 54(8): 3179-318.

Document 8: International Publication No. WO 2005/063293.

SUMMARY OF INVENTION

Technical Problem

With the method of inhibiting the phosphorylation of an SR protein using an inhibitor of an SR protein kinase (for example, see Documents 7 and 8), it is difficult to regulate the activity of a specific SR protein, and there is a possibility that the activities of all SR proteins are inhibited.

SRp30c is known to be involved in the splicing for gonadotropin receptors in addition to the splicing for GR. Therefore, even if only the activity of SRp30c were inhibited, there is still a possibility that body homeostasis is disturbed by the inhibition.

In order to increase the glucocorticoid sensitivity of cells without producing side effects, a technique for selectively inhibiting the GR splice variant regulation performed by SRp30c is required.

The invention was made in view of the above circumstances.

In view of the above circumstances, a novel compound having the activity to increase the glucocorticoid sensitivity of cells is required.

Solution to Problem

Specific means for solving the problem include those described below.

<1> An oligonucleotide that inhibits binding of a serine/arginine-rich protein 30c (SRp30c) to a pre-mRNA of a glucocorticoid receptor gene in vivo.

<2> The oligonucleotide according to <1>, wherein the oligonucleotide has a base sequence that has a length of from 15 to 50 bases and that is complementary to a continuous part of a base sequence represented by SEQ ID NO: 22.

<3> The oligonucleotide according to <2>, wherein the continuous part of the base sequence represented by SEQ ID NO: 22 has a total molar proportion of adenine and guanine of 50% or higher.

<4> The oligonucleotide according to <1>, wherein the oligonucleotide is an oligonucleotide having a base sequence represented by SEQ ID NO: 1, an oligonucleotide having a base sequence represented by SEQ ID NO: 2, an oligonucleotide having a base sequence represented by SEQ ID NO: 3, an oligonucleotide having a base sequence represented by SEQ ID NO: 4, or an oligonucleotide having a base sequence represented by SEQ ID NO: 5.

<5> A glucocorticoid sensitivity enhancer including, as an active ingredient, at least one of the oligonucleotides according to <1> to <4>.

<6> A pharmaceutical composition including at least one of the oligonucleotides according to <1> to <4>.

<7> An expression vector including at least one of the oligonucleotides according to <1> to <4>.

Advantageous Effects

According to the invention, an oligonucleotide having the activity to increase the glucocorticoid sensitivity of cells is provided.

Furthermore, according to the invention, a glucocorticoid sensitivity enhancer that includes the oligonucleotide as an active ingredient is provided.

According to the invention, a pharmaceutical composition that includes the oligonucleotide is provided.

Furthermore, according to the invention, an expression vector that expresses the oligonucleotide is provided.

DESCRIPTION OF EMBODIMENTS

Figure 1:
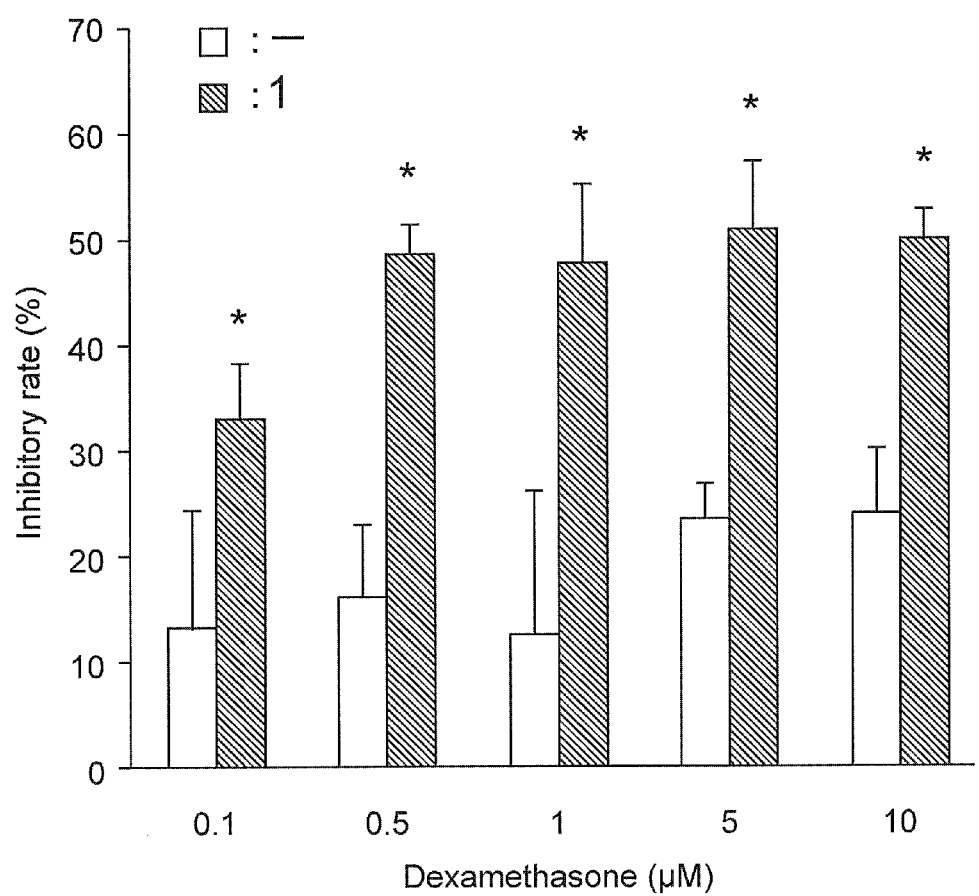
FIG. 1 is a graph showing the cell proliferation inhibitory rate in Example 2.
Figure 2:
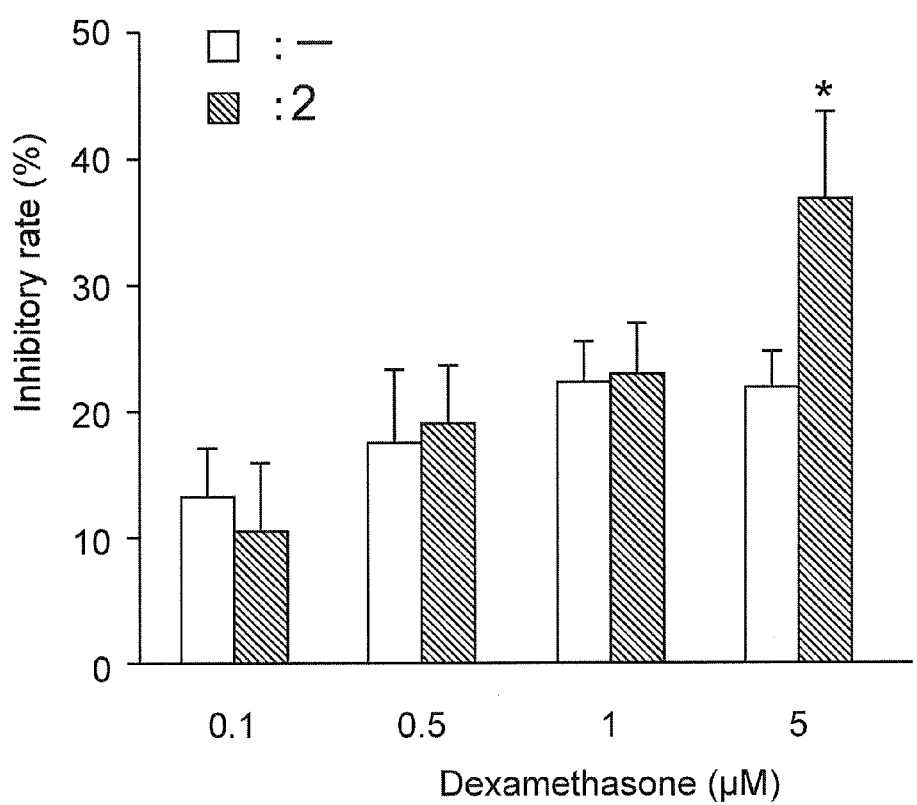
FIG. 2 is a graph showing the cell proliferation inhibitory rate in Example 2.
Figure 3:
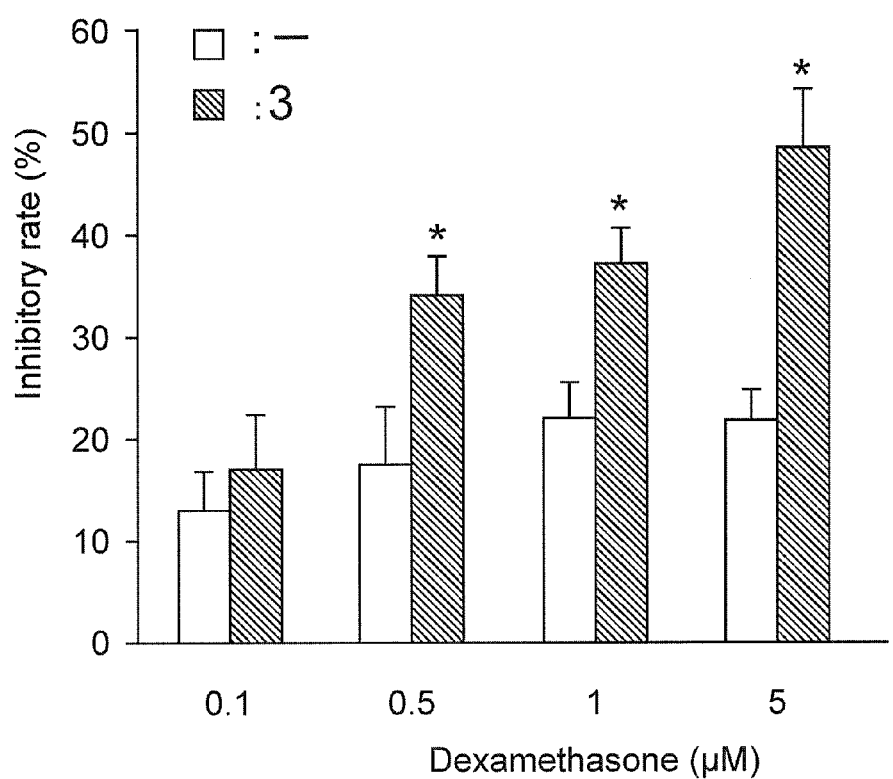
FIG. 3 is a graph showing the cell proliferation inhibitory rate in Example 2.
Figure 4:
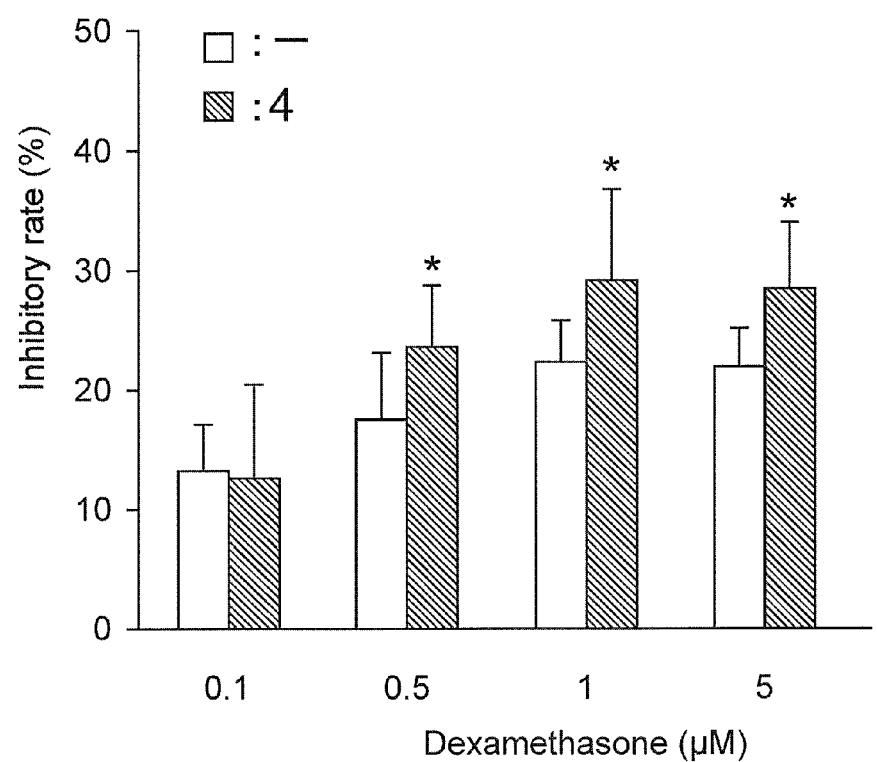
FIG. 4 is a graph showing the cell proliferation inhibitory rate in Example 2.
Figure 5:
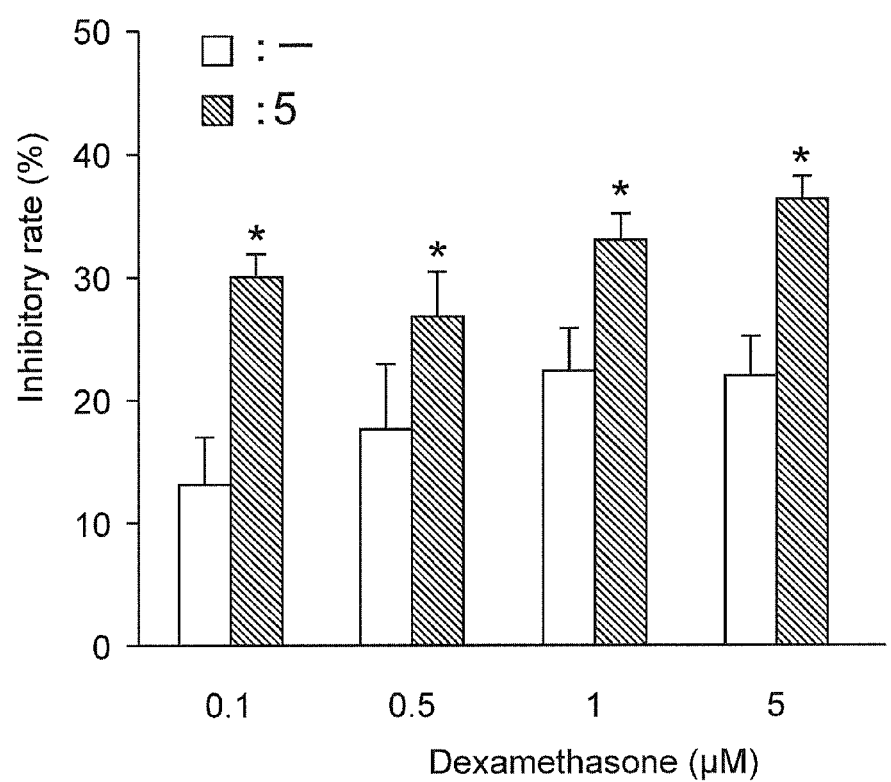
FIG. 5 is a graph showing the cell proliferation inhibitory rate in Example 2.

In the following, embodiments of the invention are sequentially described. Here, the following description and examples merely illustrate the invention, and do not limit the scope of the invention.

In this specification, each numerical range specified using "(from) . . . to . . . " represents a range including the numerical values noted before and after "to" as the minimum value and the maximum value, respectively.

Oligonucleotide

The oligonucleotide according to the invention is an oligonucleotide that inhibits the binding of a serine/arginine-rich protein 30c (SRp30c) to a pre-mRNA of a glucocorticoid receptor gene (GR gene) in vivo.

It is presumable that the oligonucleotide inhibits a glucocorticoid receptor (GR) pre-mRNA from being spliced into a mature GRβ mRNA, thereby increasing the expression level of GRα relative to that of GRβ. It is presumable that the glucocorticoid sensitivity of cells resultantly increases.

A base sequence that is a continuous part of exon 9 of the GR pre-mRNA and that has a total molar proportion of adenine (A) and guanine (B) of 50% or higher is a candidate for the site which is located in exon 9 of the GR pre-mRNA and to which SRp30c binds (splicing element).

It is thought that SR proteins tend to bind to base sequences that are rich in A and/or G Therefore, it is conceivable that SRp30c, which is a type of SR protein, is also tends to bind to A and/or G-rich sequences. Accordingly, it is highly probable that the base sequence that is a continuous part of exon 9 of the GR pre-mRNA and that has a total molar proportion of adenine and guanine of 50% or higher is the splicing element.

For the reasons discussed above, a base sequence having a length of, for example, from 15 to 50 bases and a total molar proportion of adenine and guanine of 50% or higher (preferably 60% or higher) may be selected from exon 9 of the human GR gene (NR3C1, Gene ID: 2908, NCBI Reference Sequence: NC_000005.9), and a base sequence that is complementary to the selected base sequence and that has a length of from 15 to 50 bases may be employed as the oligonucleotide according to the invention.

It is presumable that this oligonucleotide binds to the GR pre-mRNA in such a manner that the oligonucleotide completely or partially overlaps with the splicing element, or binds to the GR pre-mRNA at a position sufficiently close to the splicing element. It is presumable that the binding of the oligonucleotide inhibits binding between SRp30c and the splicing element, and inhibits the formation of the mature GRβ mRNA, as a result of which the expression level of GRα relative to GRβ increases. It is further presumable that, as a result of this, the glucocorticoid sensitivity of cells increases.

The base sequence represented by SEQ ID NO: 22 corresponds to base numbers 156091 to 157582 of the human GR gene; that is, the base sequence corresponds to a part of exon 9 of the human GR gene (from 2620th base to 4111th base from the 5'-end of exon 9). GRβ is a protein translated from a mature mRNA formed by joining together of exons 1 to 8 and a part of exon 9 (from 2631st base to 4111th base from the 5'-end of exon 9 in human) of the GR pre-mRNA are linked. Therefore, it is conceivable that the splicing element is present within the base sequence of the human GR pre-mRNA sequence represented by SEQ ID NO: 22.

In view of the above, it is preferable that the oligonucleotide according to the invention has a base sequence that has a length of from 15 to 50 bases and that is complementary to a continuous part of the base sequence represented by SEQ ID NO: 22.

It is more preferable that the oligonucleotide according to the invention has a base sequence having a length of from 15 to 50 bases and being complementary to a base sequence that is a continuous part of the base sequence represented by SEQ ID NO: 22 and that has a total molar proportion of adenine and guanine of 50% or higher (more preferably 60% or higher).

The oligonucleotide according to the invention is preferably any one of the following oligonucleotide 1, the following oligonucleotide 2, the following oligonucleotide 3, the following oligonucleotide 4, or the following oligonucleotide 5. Each of oligonucleotides 1 to 5 has the activity to increase the glucocorticoid sensitivity of cells.

Oligonucleotide 1: an oligonucleotide having a base sequence represented by SEQ ID NO: 1 (5'-CTTTCTG-GTTTTAACCACATAACATTCTATA-3').

The base sequence represented by SEQ ID NO: 1 is complementary to a continuous part of exon 9 of the human GR gene (from 2626th base to 2656th base from the 5'-end of exon 9).

Oligonucleotide 2: an oligonucleotide having a base sequence represented by SEQ ID NO: 2 (5'-AAAAGGGCA-CAGCTTCTTTTCCCATTTAATGAAA-3').

The base sequence represented by SEQ ID NO: 2 is complementary to a continuous part of exon 9 of the human GR gene (from 2796th base to 2829th base from the 5'-end of exon 9).

Oligonucleotide 3: an oligonucleotide having a base sequence represented by SEQ ID NO: 3 (5'-TAAGAT-GACTTTCTTTTCCCCCACGTATCCT-3').

The base sequence represented by SEQ ID NO: 3 is complementary to a continuous part of exon 9 of the human GR gene (from 2830th base to 2860th base from the 5'-end of exon 9).

Oligonucleotide 4: an oligonucleotide having a base sequence represented by SEQ ID NO: 4 (5'-TTTGTC-CCCATTATATAGCATTT-3').

The base sequence represented by SEQ ID NO: 4 is complementary to a continuous part of exon 9 of the human GR gene (from 3730th base to 3752nd base from the 5'-end of exon 9).

Oligonucleotide 5: an oligonucleotide having a base sequence represented by SEQ ID NO: 5 (5'-CAGATTTTTT-TATTATGATGT-3').

The base sequence represented by SEQ ID NO: 5 is complementary to a continuous part of exon 9 of the human GR gene (from 4080th base to 4100th base from the 5'-end of exon 9).

Each of oligonucleotides 1 to 5 presumably binds to the GR pre-mRNA in such a manner that the oligonucleotide completely or partially overlaps with the splicing element, or binds to the GR pre-mRNA at a position sufficiently close to the splicing element. It is conceivable that the binding of the oligonucleotide inhibits binding between SRp30c and the splicing element and inhibits generation of mature GRβ mRNA, thereby increasing the expression level GRα relative to GRβ. It is presumable that this results in an increase in the glucocorticoid sensitivity of cells.

Due to the base sequences of oligonucleotides 1 to 5, it is presumable that each of oligonucleotides 1 to 5 binds to a specific site of exon 9 of the GR pre-mRNA in a sequence specific manner. Therefore, it is conceivable that oligonucleotides 1 to 5 do not cause effects on the functions of SR proteins other than SRp30c, and do not cause effects on SRp30-regulated splicings other than the splicing of exon 9 of GR.

The scope of the oligonucleotide according to the invention encompasses an oligonucleotide having homology with oligonucleotide 1, oligonucleotide 2, oligonucleotide 3, oligonucleotide 4, or oligonucleotide 5.

The oligonucleotide having homology with oligonucleotide 1, for example, should exert an effect approximately equivalent to that of oligonucleotide 1, and is not limited in other respects. The oligonucleotide having homology with oligonucleotide 1 preferably has a homology of 80% or higher with oligonucleotide 1, more preferably has a homology of 90% or higher with oligonucleotide 1, and still more preferably has a homology of 95% or higher with oligonucleotide 1. The same shall apply to oligonucleotides having homology with any one of oligonucleotide 2, oligonucleotide 3, oligonucleotide 4, or oligonucleotide 5.

The homology can be determined, for example, by comparison of sequences utilizing a commonly-used homology search algorithm BLAST (Basic Local Alignment Search Tool) (NCBI, or Altschul, S. F. et al. J. Mol. Biol., 215:403-410 (1990)).

The scope of the oligonucleotide according to the invention includes oligonucleotides that hybridize with an oligonucleotide having a base sequence complementary to SEQ ID NO: 1 under a stringent condition and that exert an effect approximately equivalent to that of oligonucleotide 1.

The length of the oligonucleotide that hybridizes with an oligonucleotide having a base sequence complementary to SEQ ID NO: 1 under a stringent condition is not particularly limited as long as the oligonucleotide exerts an effect approximately equivalent to that of oligonucleotide 1. The oligonucleotide preferably has a length of from 15 to 45 bases. A length of the oligonucleotide of 15 bases or more suppresses sequence-nonspecific binding, and provides high stability of binding with a target mRNA. A length of the oligonucleotide of 45 bases or fewer makes it easy for the oligonucleotide to transfer into cells or nuclei. From the above points of view, the length of the oligonucleotide is more preferably a length of from 20 to 40 bases, still more preferably a length of from 22 to 38 bases, yet more preferably a length of from 23 to 35 bases, and most preferably a length of from 24 to 30 bases.

The scope of the oligonucleotide according to the invention includes oligonucleotides that hybridize with an oligonucleotide having a base sequence complementary to SEQ ID NO: 2 under a stringent condition and that exert an effect approximately equivalent to that of oligonucleotide 2.

The length of the oligonucleotide that hybridizes with an oligonucleotide having a base sequence complementary to SEQ ID NO: 2 under a stringent condition is not particularly limited as long as the oligonucleotide exerts an effect approximately equivalent to that of oligonucleotide 2. The length of the oligonucleotide is preferably a length of from 15 to 50 bases. A length of the oligonucleotide of 15 bases or more suppresses sequence non-specific binding, and provides high stability of binding with a target mRNA. A length of the oligonucleotide of 50 bases or fewer makes it easy for the oligonucleotide to transfer into cells or nuclei. From the above points of view, the length of the oligonucleotide is more preferably from a length of 20 to 45 bases, still more preferably a length of from 25 to 40 bases, yet more preferably a length of from 28 to 38 bases, and most preferably a length of from 30 to 34 bases.

The scope of the oligonucleotide according to the invention includes oligonucleotides that hybridize with an oligonucleotide having a base sequence complementary to SEQ ID NO: 3 under a stringent condition and that exert an effect approximately equivalent to that of oligonucleotide 3.

The length of the oligonucleotide that hybridizes with an oligonucleotide having a base sequence complementary to SEQ ID NO: 3 under a stringent condition is not particularly limited as long as the oligonucleotide exerts an effect approximately equivalent to that of oligonucleotide 3. The length of the oligonucleotide is preferably a length of from 15 to 45 bases. A length of the oligonucleotide of 15 bases or more suppresses sequence non-specific binding, and provides high stability of binding with a target mRNA. A length of the oligonucleotide of 45 bases or fewer makes it easy for the oligonucleotide to transfer into cells or nuclei. From the above points of view, the length of the oligonucleotide is more preferably a length of from 20 to 40 bases, still more preferably a length of from 22 to 38 bases, yet more preferably a length of from 23 to 35 bases, and most preferably a length of from 24 to 30 bases.

The scope of the oligonucleotide according to the invention includes oligonucleotides that hybridize with an oligonucleotide having a base sequence complementary to SEQ ID NO: 4 under a stringent condition and that exert an effect approximately equivalent to that of oligonucleotide 4.

The length of the oligonucleotide that hybridizes with an oligonucleotide having a base sequence complementary to SEQ ID NO: 4 under a stringent condition is not particularly limited as long as the oligonucleotide exerts an effect approximately equivalent to that of oligonucleotide 4. The length of the oligonucleotide is preferably a length of from 12 to 35 bases. A length of the oligonucleotide of 12 bases or more suppresses sequence non-specific binding, and provides high stability of binding with a target mRNA. A length of the oligonucleotide of 35 bases or fewer makes it easy for the oligonucleotide into cells or nuclei. From the above points of view, the length of the oligonucleotide is more preferably a length of from 15 to 32 bases, still more preferably a length of from 18 to 30 bases, yet more preferably a length of from 20 to 28 bases, and most preferably a length of from 22 to 25 bases.

The scope of the oligonucleotide according to the invention includes oligonucleotides that hybridize with an oligonucleotide having a base sequence complementary to SEQ ID NO: 5 under a stringent condition and that exert an effect approximately equivalent to that of oligonucleotide 5.

The length of the oligonucleotide that hybridizes with an oligonucleotide having a base sequence complementary to SEQ ID NO: 5 under a stringent condition is not particularly limited as long as the oligonucleotide exerts an effect approximately equivalent to that of oligonucleotide 5. The length of the oligonucleotide is preferably a length of from 12 to 35 bases. A length of the oligonucleotide of 12 bases or more suppresses sequence non-specific binding, and provides high stability of binding with a target mRNA. A length of the oligonucleotide of 35 bases or fewer makes it easy for the oligonucleotide to transfer into cells or nuclei. From the above points of view, the length of the oligonucleotide is more preferably a length of from 15 to 30 bases, still more preferably a length of from 16 to 25 bases, yet more preferably a length of from 18 to 23 bases, and most preferably a length of from 20 to 22 bases.

The hybridization of the oligonucleotide can be performed according to known methods or methods comparable thereto, such as the methods described in Molecular Cloning, 2nd ed. (J. Sambrook et al., Cold Spring Harbor Lab. Press, 1989).

The above-mentioned stringent condition refers to, for example, a condition with a sodium concentration of from about 19 mM to about 40 mM, preferably from about 19 mM to about 20 mM, and a temperature of from about 50° C. to about 70° C., preferably from about 60° C. to about 65° C. The condition is more preferably a condition with a sodium concentration of about 19 mM and a temperature of about 65° C.

The scope of the oligonucleotide according to the invention includes an oligonucleotide obtained from any one of oligonucleotide 1, oligonucleotide 2, oligonucleotide 3, oligonucleotide 4, or oligonucleotide 5 by deletion, substitution, or addition of one or more bases.

For example, the oligonucleotide obtained from oligonucleotide 1 by deletion, substitution, or addition of one or more bases should exert an effect approximately equivalent to that of oligonucleotide 1, and the position of the deletion, substitution, or addition is not particularly limited. The same applies to the oligonucleotide obtained from any one of oligonucleotide 2, oligonucleotide 3, oligonucleotide 4, or oligonucleotide 5 by deletion, substitution, or addition of one or more bases.

The number of bases to be deleted from oligonucleotide 1 may be one base, or two or more bases. The number of bases to be deleted from oligonucleotide 1 is, for example, from 1 base to 15 bases, preferably from 1 base to 10 bases, and more preferably from 1 base to 5 bases. The number of bases to be introduced to oligonucleotide 1 by substitution may be one base, or two or more bases. The number of bases to be introduced to oligonucleotide 1 by substitution is, for example, from 1 base to 10 bases, preferably 1 base to 5 bases, and more preferably 1 base or 2 bases. The number of bases to be added to oligonucleotide 1 may be one base, or two or more bases. The number of bases to be added to oligonucleotide 1 is, for example, from 1 base to 15 bases, preferably from 1 base to 10 bases, and more preferably from 1 base to 5 bases.

The length of the oligonucleotide obtained from oligonucleotide 1 by deletion, substitution, or addition of one or more bases is not particularly limited as long as the oligonucleotide exerts an effect approximately equivalent to that of oligonucleotide 1. The length of the oligonucleotide is preferably a length of from 20 to 40 bases. A length of the oligonucleotide of 20 bases or more suppresses sequence non-specific binding, and provides high stability of binding with a target mRNA. A length of the oligonucleotide of 40 bases or fewer makes it easy for the oligonucleotide to transfer into cells or nuclei. From the above points of view, the length of the oligonucleotide is more preferably a length of from 22 to 38 bases, still more preferably from 23 to 35 bases, and yet more preferably from 24 to 30 bases.

The number of bases to be deleted from oligonucleotide 2 may be one base, or two or more bases. The number of bases to be deleted from oligonucleotide 2 is, for example, from 1 base to 15 bases, preferably from 1 base to 10 bases, and more preferably from 1 base to 5 bases. The number of bases to be introduced into oligonucleotide 2 by substitution may be one base, or two or more bases. The number of bases to be introduced into oligonucleotide 2 is, for example, from 1 base to 10 bases, preferably from 1 base to 5 bases, and more preferably 1 base or 2 bases. The number of bases to be added to oligonucleotide 2 may be one base, or two or more bases. The number of bases to be added to oligonucleotide 2 is, for example, from 1 base to 15 bases, preferably from 1 base to 10 bases, and more preferably from 1 base to 5 bases.

The length of the oligonucleotide obtained from oligonucleotide 2 by deletion, substituted, or addition of one or more bases is not particularly limited as long as the oligonucleotide exerts an effect approximately equivalent to that of oligonucleotide 2. The length of the oligonucleotide is preferably a length of from 20 to 45 bases. A length of the oligonucleotide of 20 bases or more suppresses sequence non-specific binding, and provides high stability of binding with a target mRNA. A length of the oligonucleotide of 45 bases or fewer makes it easy for the oligonucleotide to transfer into cells or nuclei. From the above points of view, the length of the oligonucleotide is more preferably a length of from 25 to 40 bases, still more preferably a length of from 28 to 38 bases, and yet more preferably a length of from 30 to 34 bases.

The number of bases to be deleted from oligonucleotide 3 may be one base, or two or more bases. The number of bases to be deleted from oligonucleotide 3 is, for example, from 1 base to 15 bases, preferably from 1 base to 10 bases, and more preferably from 1 base to 5 bases. The number of bases to be introduced to oligonucleotide 3 by substitution may be one base, or two or more bases. The number of bases to be introduced to oligonucleotide 3 by substitution is, for example, from 1 base to 10 bases, preferably from 1 base to 5 bases, and more preferably 1 base or 2 bases. The number of bases to be added to oligonucleotide 3 may be one base, or two or more bases. The number of bases to be added to oligonucleotide 3 is, for example, from 1 base to 15 bases, preferably from 1 base to 10 bases, and more preferably from 1 base to 5 bases.

The length of the oligonucleotide obtained from oligonucleotide 3 by deletion, substitution, or addition of one or more bases is not particularly limited as long as the oligonucleotide exerts an effect approximately equivalent to that of oligonucleotide 3. The length of the oligonucleotide is preferably a length of from 20 to 40 bases. A length of the oligonucleotide of 20 bases or more suppresses sequence non-specific binding, and provides high stability of binding with a target mRNA. A length of the oligonucleotide of 40 bases or fewer makes it easy for the oligonucleotide to transfer into cells or nuclei. From the above points of view, the length of the oligonucleotide is more preferably from 22 to 38 bases, still more preferably from 23 to 35 bases, and yet more preferably from 24 to 30 bases.

The number of bases to be deleted from oligonucleotide 4 may be one base, or two or more bases. The number of bases to be deleted from oligonucleotide 4 is, for example, from 1 base to 15 bases, preferably from 1 base to 10 bases, and more preferably from 1 base to 5 bases. The number of bases to be introduced to oligonucleotide 4 by substitution may be one base, or two or more bases. The number of bases to be introduced to oligonucleotide 4 by substitution is, for example, from 1 base to 10 bases, preferably from 1 base to 5 bases, and more preferably 1 base or 2 bases. The number of bases to be added to oligonucleotide 4 may be one base, or two or more bases. The number of bases to be added to oligonucleotide 4 is, for example, from 1 base to 15 bases, preferably from 1 base to 10 bases, and more preferably from 1 base to 5 bases.

The length of the oligonucleotide obtained from oligonucleotide 4 by deletion, substitution, or addition of one or more bases is not particularly limited as long as the oligonucleotide exerts an effect approximately equivalent to that of oligonucleotide 4. The length of the oligonucleotide is preferably a length of from 15 to 32 bases. A length of the oligonucleotide of 15 bases or more suppresses sequence non-specific binding, and provides high stability of binding with a target mRNA. A length of the oligonucleotide of 32 bases or fewer makes it easy for the oligonucleotide to transfer into cells or nuclei. From the above points of view, the length of the oligonucleotide is more preferably from 18 to 30 bases, still more preferably from 20 to 28 bases, and yet more preferably from 22 to 25 bases.

The number of bases to be deleted from oligonucleotide 5 may be one base, or two or more bases. The number of bases to be deleted from oligonucleotide 5 is, for example, from 1 base to 15 bases, preferably from 1 base to 10 bases, and more preferably from 1 base to 5 bases. The number of bases to be introduced to oligonucleotide 5 by substitution may be one base, or two or more bases. The number of bases to be introduced to oligonucleotide 5 by substitution is, for example, from 1 base to 10 bases, preferably from 1 base to 5 bases, and more preferably 1 base or 2 bases. The number of bases to be added to oligonucleotide 5 may be one base, or two or more bases. The number of bases to be added to oligonucleotide 5 is, for example, from 1 base to 15 bases, preferably from 1 base to 10 bases, and more preferably from 1 base to 5 bases.

The length of the oligonucleotide obtained from oligonucleotide 5 by deletion, substitution, or addition of one or more bases is not particularly limited as long as the oligonucleotide exerts an effect approximately equivalent to that of oligonucleotide 5. The length of the oligonucleotide is preferably a length of from 15 to 30 bases. A length of the oligonucleotide of 15 bases or more suppresses sequence non-specific binding, and provides high stability of binding with a target mRNA. A length of the oligonucleotide of 30 bases or fewer makes it easy for the oligonucleotide to transfer into cells or nuclei. From the above points of view, the length of the oligonucleotide is more preferably from 16 to 25 bases, still more preferably from 18 to 23 bases, and yet more preferably from 20 to 22 bases.

The oligonucleotide according to the invention may be selected not only from an oligo-DNA or an oligo-RNA, but also from a phosphorothioate oligo-DNA or a phosphorothioate oligo-RNA.

The phosphorothioate nucleotide is a nucleotide that has a sulfur atom substituted for an oxygen atom of a phosphate group positioned at a connecting portion between nucleotide units. The phosphorothioate nucleotide is preferable since it has resistance to various nucleases, and therefore has a higher stability than nucleotides.

From the viewpoints of stability, the oligonucleotide according to the invention is preferably an oligo-DNA, and more preferably a phosphorothioate oligo-DNA.

The oligonucleotide according to the invention can be obtained by chemical synthesis in accordance with ordinary methods for oligonucleotide synthesis.

Oligonucleotide 1 can also be synthesized by PCR using a region that includes a sequence of from 2626th base to 2656th base from the 5'-end of exon 9 of the human GR gene as a template and using appropriate primers.

Oligonucleotide 2 can be synthesized by PCR using a region that includes a sequence of from 2796th base to 2829th base from the 5'-end of exon 9 of the human GR gene as a template and using appropriate primers.

Oligonucleotide 3 can be synthesized by PCR using a region that includes a sequence of from 2830th base to 2860th base from the 5'-end of exon 9 of the human GR gene as a template and using appropriate primers.

Oligonucleotide 4 can be synthesized by PCR using a region that includes a sequence of from 3730th base to 3752th base from the 5'-end of exon 9 of the human GR gene as a template and using appropriate primers.

Oligonucleotide 5 can be synthesized by PCR using a region that includes a sequence of from 4080th base to 4100th base from the 5'-end of exon 9 of the human GR gene as a template and using appropriate primers.

In the invention, the expression "the activity to increase the glucocorticoid sensitivity of cells" used in relation to an oligonucleotide refers to an activity that increases the glucocorticoid sensitivity of cells in a case in which the cells are contacted with the oligonucleotide as compared to a case in which the cells are not contacted with the oligonucleotide.

Whether or not an oligonucleotide has "the activity to increase the glucocorticoid sensitivity of cells" can be confirmed by comparing a cell proliferation rate in a case in which the cells are contacted with the oligonucleotide and glucocorticoid and a cell proliferation rate in a case in which the cells are not contacted with the oligonucleotide and glucocorticoid. For example, the oligonucleotide may be introduced into cells derived from lymphoma or lymphocytic leukemia, glucocorticoid may be added into the culture medium for the cells, and the activity to increase the glucocorticoid sensitivity can be confirmed by a decrease in the proliferation rate of the cells.

The oligonucleotide according to the invention can be transferred into cells by culturing the cells in a medium that contains the oligonucleotide. At this time, the efficiency of introduction into cells can be improved by using the oligonucleotide in mixture with LIPOFECTAMINE. The efficiency of introduction into cells can also be improved by electroporation.

Glucocorticoid Sensitivity Enhancer

The glucocorticoid sensitivity enhancer according to the invention includes, in a pharmaceutically acceptable medium, at least one oligonucleotide according to the invention as an active ingredient.

The administration of the glucocorticoid sensitivity enhancer can increase the expression level of GRα relative to GRβ. Therefore, the glucocorticoid sensitivity enhancer can be used as a drug to enhance the glucocorticoid sensitivity of the body.

The medium and additives for drug formulation used for the preparation of the glucocorticoid sensitivity enhancer are not particularly limited with respect to their types. Examples of the medium include solid media (e.g., gelatin, lactose) and liquid media (e.g., water, physiological saline, glucose aqueous solution). Examples of the additives for drug formulation include surfactants (e.g., saccharides, polyhydric alcohols, esters of polyhydric alcohols) and buffers (e.g., sodium citrate, sodium phosphate).

The glucocorticoid sensitivity enhancer is preferably includes, in a liquid medium suitable for intravenous administration, an appropriate amount of at least one of the oligonucleotide according to the invention. In this case, the administration of the glucocorticoid sensitivity enhancer is performed by intravenous injection or intravenous drip into a subject to which the glucocorticoid sensitivity enhancer is to be administered.

From the viewpoint of storage stability, the glucocorticoid sensitivity enhancer is preferably in the lyophilized state. In this case, the glucocorticoid sensitivity enhancer in the lyophilized state may be dissolved in a liquid medium before use.

The glucocorticoid sensitivity enhancer is usually used in combination with glucocorticoid, which is an adrenal cortex hormone. In cases in which the glucocorticoid sensitivity enhancer and glucocorticoid are used together, the glucocorticoid sensitivity enhancer may be administered simultaneously with the administration of glucocorticoid, or administered before or after the administration of glucocorticoid.

The glucocorticoid to be used in combination with the glucocorticoid sensitivity enhancer may be a purification product of a natural product, or a steroid agent that is an artificially synthesized product (e.g., dexamethasone, betamethasone, prednisolone, and the like).

The glucocorticoid sensitivity enhancer may be administered to any patient having conditions to which administration of a steroid agent is suitable, such as allergic diseases such as asthma or atopic dermatitis, autoimmune diseases such as rheumatism or inflammatory bowel diseases, lymphoma, or lymphocytic leukemia.

The glucocorticoid sensitivity enhancer is usable for patients who suffer from any of the above diseases and exhibit glucocorticoid resistance, and also usable for patients who suffer from any of the above diseases but do not exhibit glucocorticoid resistance. The administration to the latter patients has a benefit in that dosage of glucocorticoid can be reduced.

Although varying with the type and severity of the disease to be treated, the glucocorticoid sensitivity enhancer is preferably administered in an effective dose for an adult per administration of from 0.01 mg/kg to 100 mg/kg, and more preferably from 0.1 mg/kg to 30 mg/kg. The number of times of administration is not particularly limited, and the glucocorticoid sensitivity enhancer may be administered once, administered repeatedly, or administered continuously. The administration interval and the administration period may be selected by those skilled in the art in accordance with clinical finding, imaging finding, hematological finding, comorbidity, past medical history, and the like.

The use of the glucocorticoid sensitivity enhancer is not restricted to human use, and the glucocorticoid sensitivity enhancer may be used for farm animals such as cattle, horse, or sheep, or pet animals such as canine, cat, or monkey.

The oligonucleotide included in the glucocorticoid sensitivity enhancer as an active ingredient is preferably at least one selected from the group consisting of oligonucleotide 1, oligonucleotide 2, oligonucleotide 3, oligonucleotide 4, and oligonucleotide 5.

It is presumable that each of oligonucleotides 1 to 5 binds to a specific site of exon 9 of the GR pre-mRNA in a sequence specific manner and selectively inhibits the binding of SRp30c to the splicing element. Therefore, the administration of the glucocorticoid sensitivity enhancer that includes at least one of oligonucleotides 1 to 5 as an active ingredient to the body has low possibility of causing side effects.

Pharmaceutical Composition

The pharmaceutical composition according to the invention includes at least one of the oligonucleotide according to the invention in a pharmaceutically acceptable medium.

The pharmaceutical composition can increase the expression level of GRα relative to GRβ and can enhance the glucocorticoid sensitivity of the body.

The medium and additives for drug formulation used for the preparation of the pharmaceutical composition are not particularly limited with respect to their types. Examples of the medium and the additives for drug formulation include the above-described solid media, liquid media, surfactants, and buffers for the glucocorticoid sensitivity enhancer.

The pharmaceutical composition may be used for the treatment of various diseases or physical damages such as allergic diseases, autoimmune diseases, cancers, endocrine system diseases, psychiatric disorders, infections, or injuries. In particular, the pharmaceutical composition is favorably administered to patients having conditions to which administration of a steroid agent is suitable, such as allergic diseases, autoimmune diseases, lymphoma, or lymphocytic leukemia.

The pharmaceutical composition may be administered to a patient by a method such as intravascular administration, intravesical administration, intraperitoneal injection, or topical administration.

Accordingly, using the pharmaceutical composition, a method of treating various diseases or physical damages (such as allergic diseases, autoimmune diseases, cancers, endocrine system diseases, psychiatric disorders, infections, or injuries) is provided. The method of treating includes administering the pharmaceutical composition to a patient suffering from any of various diseases or physical damages (such as allergic diseases, autoimmune diseases, cancers, endocrine system diseases, psychiatric disorders, infections, or injuries). The scope of the term "treating" in the method of treating includes any improvement of the condition, and encompasses suppression of an increase in severity and reduction or alleviation of symptoms.

The pharmaceutical composition may be used in combination with glucocorticoid, which is an adrenal cortex hormone. When the pharmaceutical composition and glucocorticoid are used together, the pharmaceutical composition may be administered simultaneously with the administration of glucocorticoid, or administered before or after the administration of glucocorticoid.

The glucocorticoid to be used in combination with the pharmaceutical composition may be a purification product of a natural product, or a steroid agent that is an artificially synthesized product (e.g., dexamethasone, betamethasone, prednisolone, and the like).

The use of the pharmaceutical composition is not restricted for human use, and the pharmaceutical composition may be used for farm animals such as cattle, horse, or sheep, or pet animals such as canine, cat, or monkey.

The oligonucleotide included in the pharmaceutical composition is preferably at least one selected from the group consisting of oligonucleotide 1, oligonucleotide 2, oligonucleotide 3, oligonucleotide 4, and oligonucleotide 5.

It is conceivable that each of oligonucleotides 1 to 5 binds to a specific site of exon 9 of the GR pre-mRNA in a sequence specific manner and selectively inhibits the binding of SRp30c to the splicing element. Therefore, the administration of the glucocorticoid sensitivity enhancer that includes at least one of oligonucleotides 1 to 5 as an active ingredient to the body has low possibility of side effects.

Expression Vector

The expression vector according to the invention includes the oligonucleotide according to the invention, and is used for the expression of the oligonucleotide according to the invention. The expression vector can be obtained by inserting, into a freely-selected vector, a double-stranded oligonucleotide (preferably a double-stranded DNA) that includes the oligonucleotide according to the invention (preferably DNA) in one of the strands.

The vector into which the double-stranded nucleotide is to be inserted is not particularly limited as long as the vector can replicate in the host cell, and examples thereof include plasmid DNAs and phage DNAs. Examples of the plasmid DNAs include plasmids derived from *Escherichia coli* (e.g., pBR322, pBR325, pUC118, pUC119, pUC18, pUC19, and the like), plasmids derived from *Bacillus subtilis* (e.g., pUB110, pTPS, and the like), and plasmids derived from yeasts (e.g., YEp13, YEp24, YCp50, and the like). Examples of the phage DNAs include lambda phage DNAs (e.g., Charon4A, Charon 21A, EMBL3, EMBL4, λgt10, λgt11, λZAP, and the like). Vectors derived from animal viruses such as retroviruses or vaccinia viruses, and vectors derived from insect viruses such as baculoviruses are usable.

The double-stranded nucleotide that includes oligonucleotide 1 in one of the strands can be synthesized by, for example, PCR using 2626th to 2656th bases from the 5'-end of exon 9 of the human GR gene as a template and using primers containing appropriate restriction sites.

The double-stranded nucleotide that includes oligonucleotide 2 in one of the strands can be synthesized by, for example, PCR using 2796th to 2829th bases from the 5'-end of exon 9 of the human GR gene as a template and using primers containing appropriate restriction sites.

The double-stranded nucleotide that includes oligonucleotide 3 in one of the strands can be synthesized by, for example, PCR using 2830th to 2860th bases from the 5'-end of exon 9 of the human GR gene as a template and using primers containing appropriate restriction sites.

The double-stranded nucleotide that includes oligonucleotide 4 in one of the strands can be synthesized by, for example, PCR using 3730th to 3752th bases from the 5'-end of exon 9 of the human GR gene as a template and using primers containing appropriate restriction sites.

The double-stranded nucleotide that includes oligonucleotide 5 in one of the strands can be synthesized by, for example, PCR using 4080th to 4100th bases from the 5'-end of exon 9 of the human GR gene as a template and using primers containing appropriate restriction sites.

Further, the double-stranded nucleotide thus obtained may be digested with an appropriate restriction enzyme and inserted to a restriction site or a multicloning site of an appropriate vector, whereby the expression vector can be obtained.

EXAMPLES

Hereinafter, the invention is described more specifically with reference to examples. The invention is not limited to the following examples as long as the gist of the invention is retained.

Example 1

Examination of GRα and GRβ Expression Levels

Preparation of Oligonucleotide

As oligonucleotides to be introduced into cells, oligonucleotide 1, oligonucleotide 2, oligonucleotide 3, oligonucleotide 4, and oligonucleotide 5 were prepared. These oligonucleotides were prepared by conventional chemical synthesis. The base sequences thereof are shown in Table 1.

TABLE 1

| | Oligonucleotide Sequence (5'→3') | Corresponding position in exon 9 | Number of bases | SEQ ID NO |
|---|---|---|---|---|
| 1 | CTTTCTGGTT TTAACCACAT AACATTCTAT A | 2626 to 2656 | 31 | 1 |
| 2 | AAAAGGGCAC AGCTTCTTTT CCCATTTAAT GAAA | 2796 to 2829 | 34 | 2 |
| 3 | TAAGATGACT TTCTTTTCCC CCACGTATCC T | 2830 to 2860 | 31 | 3 |
| 4 | TTTGTCCCCA TTATATAGCA TTT | 3730 to 3752 | 23 | 4 |
| 5 | CAGATTTTTT TATTATGATG T | 4080 to 4100 | 21 | 5 |

In Table 1, "Corresponding position in exon 9" is a position in exon 9 of the human GR gene (having 4110 bases) at which a sequence complementary to the oligonucleotide of interest is present (the base number being counted from the 5'-end of exon 9). More specifically, the base sequence of oligonucleotide 1, for example, is a base sequence complementary to the base sequence of from 2626th to 2656th bases from the 5'-end of exon 9 of the human GR gene.

Cell Culture

Raji cells (manufactured by Japan Health Science Foundation) derived from human Burkitt's lymphoma were used in experiments.

Raji cells were cultured and maintained in RPMI1640 medium (manufactured by Gibco) at 37° C. in an atmosphere of 5% $CO_2$, the RPMI1640 medium being supplemented with 10% fetal bovine serum (FBS) (manufactured by Filtoron), 100 U/ml penicillin, and 100 µg/ml streptomycin.

Introduction of Oligonucleotide into Cells $2 \times 10^6$ Raji cells were washed with phosphate-buffered saline (PBS) and suspended in 100 µl transfection reagent of an Amaxa cell line Nucleofector Kit V (manufactured by Lonza). The oligonucleotide was add to a concentration of 300 nM, and introduction into the cells was immediately carried out by electroporation using a Nucleofector I device (manufactured by Lonza).

In the experiments for checking the concentration dependency, the concentration of the oligonucleotide was set to varied concentrations of 5 nM, 10 nM, 50 nM, 100 nM, and 500 nM.

After the Raji cells were cultured in the above-described medium for 24 hours, the Raji cells were used for subsequent experiments.

Measurement of GRα and GRβ Expression Levels

The expressions levels of GRα and GRβ in the Raji cells to which the oligonucleotide had been introduced was determined by RT-PCR and PCR. The expression level of glyceraldehyde-3-phosphate dehydrogenase (GAPDH) was determined as an endogenous control.

After the Raji cells were washed with PBS, RNA was extracted using a FastPure RNA Kit (manufactured by Takara Bio Inc.), and reverse transcription was performed using a PrimeScript 1st strand cDNA synthesis kit (manufactured by Takara Bio Inc.). The obtained cDNA was amplified using Platinum Taq DNA polymerase (manufactured by Invitrogen) and PCR primers (having the base sequences shown in Table 2) specific for the gene of interest. The PCR conditions included: performing initial denaturation at 94° C. for 2 minutes; performing 35 cycles of denaturation (94° C. for 30 seconds), annealing (55° C. for 30 seconds), and extension (72° C. for 1 minute); and then performing final extension at 72° C. for 4 minutes.

TABLE 2

| Intended Use | Name | Base Sequence (5'→3') | SEQ ID NO |
|---|---|---|---|
| GRα detection primers | GRα-Fw | CTATGCATGA AGTGGTTGAA AA | 6 |
| | GRα-Rv | TTTCAGCTAA CATCTCGGG | 7 |
| GRβ detection primers | GRβ-Fw | GAAGGAAACT CCAGCCAGAA | 8 |
| | GRβ-Rv | CCACATAACA TTTTCATGCA TAGA | 9 |
| GAPDH detection primers | GAPDH-Fw | ATGGCCTTCC GTGTTCCTAC | 10 |
| | GAPDH-Rv | TGATGTCATC ATACTTGGCA GG | 11 |

After the PCR was performed, DNA was separated by two-dimensional electrophoresis on a 2% agarose gel containing ethidium bromide, and the intensity of bands was quantified using an image analyzer GEL PRINT 2000i/VGA (manufactured by Genomic Solutions).

The expression levels of GAPDH, GRα, and GRβ in the Raji cells transfected with any one of oligonucleotides 1 to 5 are shown in Table 3. In Table 3, "relative value of GRα/GRβ" means a relative value assuming that "the value obtained by dividing the expression level of GRα by the expression level GRβ" in cells not transfected with the oligonucleotide is 1.

The expression levels of GAPDH, GRα, and GRβ in the Raji cells transfected with various concentrations of oligonucleotide 1 are shown in Table 4.

Each experiment was performed in triplicate. The values noted in Tables 3 and 4 are average values of the three experiments.

TABLE 3

| Oligonucleotide | GAPDH | GRα | GRβ | GRα/ GAPDH | GRβ/ GAPDH | Relative value of GRα/GRβ |
|---|---|---|---|---|---|---|
| — | 2927.753 | 2742.743 | 4686.844 | 0.938 | 1.600 | 1 |
| 1 | 3033.167 | 3278.767 | 4611.084 | 1.082 | 1.519 | 1.213 |
| 2 | 3169.938 | 3340.440 | 4641.922 | 1.054 | 1.467 | 1.226 |
| 3 | 3128.467 | 3177.814 | 4596.457 | 1.015 | 1.471 | 1.182 |
| 4 | 2991.776 | 3157.440 | 4592.806 | 1.057 | 1.533 | 1.173 |
| 5 | 3087.403 | 3210.228 | 4516.989 | 1.041 | 1.461 | 1.210 |

TABLE 4

| | Addition amount [μM] of oligonucleotide 1 | | | | | |
|---|---|---|---|---|---|---|
| | 0 | 5 | 10 | 50 | 100 | 500 |
| GAPDH | 3199.355 | 3255.648 | 3125.355 | 2754.991 | 2861.698 | 2974.113 |
| GRα | 2838.719 | 2945.841 | 2745.770 | 2992.790 | 2655.770 | 2626.527 |
| GRβ | 4032.255 | 3634.619 | 3284.891 | 3244.062 | 3306.770 | 3117.062 |
| GRα/GAPDH | 0.887 | 0.905 | 0.879 | 1.086 | 0.928 | 0.883 |
| GRβ/GAPDH | 1.260 | 1.116 | 1.051 | 1.178 | 1.156 | 1.048 |
| GRα/GRβ | 0.704 | 0.810 | 0.836 | 0.923 | 0.803 | 0.843 |

As is apparent from Table 3, "relative value of GRα/GRβ" exceeded 1.1 in the cells to which any one of oligonucleotides 1 to 5 was introduced. This result suggests the possibility that the introduction of these oligonucleotides into the cells increases the glucocorticoid sensitivity of cells.

As is apparent from Table 4, oligonucleotide 1 decreased the expression level of GRβ in a concentration-dependent manner.

Example 2

Examination of Glucocorticoid Sensitivity of Oligonucleotide-Transfected Cells

Cells Transfected with Oligonucleotide 1

In order to examine the change of glucocorticoid sensitivity of cells caused by introduction of oligonucleotide 1, cell proliferation was quantified by a 5-bromo-2'-deoxyuridine (BrdU) incorporation assay. Dexamethasone (manufactured by Biomol) was used as a glucocorticoid. The concentration of dexamethasone was set to varied concentrations of 0 μM (no addition), 0.1 μM, 0.5 μM, 1 μM, 5 μM, and 10 μM.

Raji cells were cultured in serum-free RPMI1640 medium for 12 hours to synchronize the cell cycle, and then re-suspended in RPMI1640 medium supplemented with serum and inoculated onto a 96-well plate.

After dexamethasone was added, the cells were cultured for 22 hours. Then, BrdU was added thereto, and the cells were cultured for another 2 hours. After centrifugation, the supernatant was discarded, and the cells were dried and fixed. The fixed cells were allowed to react with a peroxidase-labeled anti-BrdU antibody for 1 hour at room temperature. Subsequently, the cells were washed three times with PBS, and tetramethylbenzidine was added thereto. When noticeable coloring was observed, the reaction was stopped by adding $H_2SO_4$ (1M). After vigorous agitation, absorbance at 450 nm was measured using a plate reader. The results are shown in Table 5.

Using the Raji cells to which dexamethasone was not added as a control, cell proliferation inhibitory rate (%) was calculated based on the relative ratio of the obtained absorbance. The results are shown in Table 6 and FIG. 1. Here, statistical significance was assessed with one-way analysis of variance and multiple comparison. Tukey's multiple comparison was used for the multiple comparison. A significance level of $P<0.05$ (vs. no addition of oligonucleotide) was regarded as a significant difference.

Each experiment was performed in triplicate. The values noted in Tables 5 and 6 are average values of the three experiments.

TABLE 5

| Oligonucleotide introduced | | — | | | | | |
|---|---|---|---|---|---|---|---|
| Addition amount [μM] of dexamethasone | | 0 | 0.1 | 0.5 | 1 | 5 | 10 |
| BrdU incorporation | Average | 0.552 | 0.475 | 0.461 | 0.479 | 0.422 | 0.418 |
| | SE | 0.015 | 0.049 | 0.026 | 0.064 | 0.013 | 0.023 |
| Oligonucleotide introduced | | Oligonucleotide 1 | | | | | |
| Addition amount [μM] of dexamethasone | | 0 | 0.1 | 0.5 | 1 | 5 | 10 |
| BrdU incorporation | Average | 0.556 | 0.372 | 0.286 | 0.292 | 0.271 | 0.279 |
| | SE | 0.026 | 0.030 | 0.013 | 0.047 | 0.024 | 0.005 |

TABLE 6

| Oligonucleotide introduced | | — | | | | |
|---|---|---|---|---|---|---|
| Addition amount [μM] of dexamethasone | | 0.1 | 0.5 | 1 | 5 | 10 |
| cell proliferation inhibitory rate | Average [%] | 13.445 | 16.217 | 12.647 | 23.343 | 23.877 |
| | SE | 11.108 | 6.713 | 13.622 | 3.532 | 6.240 |
| Oligonucleotide introduced | | Oligonucleotide 1 | | | | |
| Addition amount [μM] of dexamethasone | | 0.1 | 0.5 | 1 | 5 | 10 |
| cell proliferation inhibitory rate | Average [%] | 32.874 | 48.364 | 47.553 | 50.624 | 49.526 |
| | SE | 5.620 | 3.005 | 7.501 | 6.646 | 2.988 |

As is apparent from Tables 5 and 6 and FIG. 1, in Raji cells transfected with oligonucleotide 1, the addition of dexamethasone resulted in a significant reduction in BrdU incorporation and a significant increase in cell proliferation inhibitory rate, compared to Raji cells not transfected with the oligonucleotide. These results indicate that the introduction of oligonucleotide 1 increased the glucocorticoid sensitivity of cells.

Therefore, according to the invention, an oligonucleotide having the activity to increase the glucocorticoid sensitivity of cells can be provided.

Cells Transfected with Oligonucleotide 2, 3, 4, or 5

BrdU incorporation assay was performed in the same manner as in the above, and alternation of the glucocorticoid sensitivity of the cells caused by the introduction of any one of oligonucleotides 2 to 5 was examined. The cell proliferation inhibitory rates (%) were shown in Table 7 and FIGS. 2 to 5. Each experiment was carried out in quadruplicate. The values shown in Table 7 are average values thereof.

TABLE 7

| Oligonucleotide transfected | | — | | | |
|---|---|---|---|---|---|
| Additive amount [μM] of dexamethasone | | 0.1 | 0.5 | 1 | 5 |
| cell proliferation inhibitory rate | Average [%] | 13.184 | 17.615 | 22.210 | 21.718 |
| | SE | 3.691 | 5.538 | 3.414 | 3.052 |

| Oligonucleotide transfected | | Oligonucleotide 2 | | | |
|---|---|---|---|---|---|
| Additive amount [μM] of dexamethasone | | 0.1 | 0.5 | 1 | 5 |
| cell proliferation inhibitory rate | Average [%] | 10.541 | 19.044 | 22.769 | 36.402 |
| | SE | 5.440 | 4.688 | 4.165 | 7.216 |

| Oligonucleotide transfected | | Oligonucleotide 3 | | | |
|---|---|---|---|---|---|
| Additive amount [μM] of dexamethasone | | 0.1 | 0.5 | 1 | 5 |
| cell proliferation inhibitory rate | Average [%] | 16.924 | 34.134 | 37.164 | 48.256 |
| | SE | 5.330 | 3.814 | 3.389 | 5.871 |

| Oligonucleotide transfected | | Oligonucleotide 4 | | | |
|---|---|---|---|---|---|
| Additive amount [μM] of dexamethasone | | 0.1 | 0.5 | 1 | 5 |
| cell proliferation inhibitory rate | Average [%] | 12.464 | 23.397 | 28.863 | 28.061 |
| | SE | 8.029 | 5.302 | 7.617 | 5.887 |

| Oligonucleotide transfected | | Oligonucleotide 5 | | | |
|---|---|---|---|---|---|
| Additive amount [μM] of dexamethasone | | 0.1 | 0.5 | 1 | 5 |
| cell proliferation inhibitory rate | Average [%] | 29.842 | 26.632 | 32.895 | 36.053 |
| | SE | 2.049 | 3.688 | 2.101 | 1.926 |

As is apparent from Table 7 and FIGS. 2 to 5, in Raji cells transfected with any one of oligonucleotides 2 to 5, the addition of dexamethasone resulted in a significant increase in cell proliferation inhibitory rate, compared to Raji cells not transfected with the oligonucleotide. These results indicate that the introduction of any one of oligonucleotides 2 to 5 increased the glucocorticoid sensitivity of cells.

Therefore, according to the invention, an oligonucleotide having the activity to increase the glucocorticoid sensitivity of cells can be provided.

Experiment 3

Examination of Estrogen Receptor Expression Level

Estrogen receptor (ER) has two splice variants: ERα and ERβ. It is known that SRp30c is involved in regulating the splicing of ER mRNA.

The expressions levels of ERα and ERβ in Raji cells transfected with oligonucleotide 1 were determined by RT-PCR and PCR.

Raji cells transfected with oligonucleotide 1 were obtained in the same manner as in "Cell Culture" and "Introduction of Oligonucleotide into Cells" in Example 1. The oligonucleotide 1 concentration at the time of introduction into cells was 300 nM.

Measurement of Estrogen Receptor Expression Level

After the Raji cells were washed with PBS, RNA was extracted using a FASTPURE RNA Kit (manufactured by Takara Bio Inc.), and reverse transcription was performed using a PRIMESCRIPT 1st strand cDNA synthesis kit (manufactured by Takara Bio). The obtained cDNA was amplified using PLATINUM Taq DNA polymerase (manufactured by Invitrogen) and PCR primers (having the sequences shown in Table 8) specific for the gene of interest. The PCR conditions included: performing an initial denaturation at 94° C. for 2 minutes; performing 35 cycles of denaturation (94° C. for 30 seconds), annealing (55° C. for 30 seconds), and extension (72° C. for 1 minute); and performing a final extension at 72° C. for 4 minutes.

The expression level of GAPDH as an endogenous control was determined using PCR primers of SEQ ID Nos: 10 and 11.

TABLE 8

| Intended use | Name | Base Sequence (5'→3') | SEQ ID NO |
|---|---|---|---|
| ERα detection primers | ERα-Fw | CCTACTACCT GGAGAACGAG | 12 |
| | ERα-Rv | CTCTTCGGTC TTTTCGTATG | 13 |
| ERβ detection primers | ERβ-Fw | AAAAGAATCA TTCAATGACA | 14 |
| | ERβ-Rv | ATTAACACCT CCATCCAACA | 15 |

After the PCR was performed, DNA was separated by two-dimensional electrophoresis on a 2% agarose gel containing ethidium bromide, and the intensity of bands was quantified using an image analyzer GEL PRINT 2000i/VGA (manufactured by Genomic Solutions Inc.).

The expression levels of GAPDH, ERα, and ERβ in the Raji cells transfected with oligonucleotide 1 are shown in Table 9. In Table 9, "relative value of ERα/ERβ" means a relative value, assuming that "the value obtained by dividing the expression level of ERα by the expression level ERβ" in cells not transfected with the oligonucleotide is 1.

TABLE 9

| Oligonucleotide | GAPDH | ERα | ERβ | ERα/GAPDH | ERβ/GAPDH | ERα/ERβ | Relative value of ERα/ERβ |
|---|---|---|---|---|---|---|---|
| — | 2832.941 | 2152.648 | 1271.527 | 0.760 | 0.449 | 1.693 | 1 |
| 1 | 2476.113 | 2201.941 | 1299.820 | 0.889 | 0.525 | 1.694 | 1.001 |

As is apparent from Table 9, "relative value of ERα/ERβ" was approximately 1 in the cells transfected with oligonucleotide 1. This results indicate that the introduction of oligonucleotide 1 into cells does not affect the regulation of the splicing of ER mRNA.

Example 4

Examination of Antitumor Effect of Oligonucleotide

Preparation of Oligonucleotide 4 Expression Vector

Oligonucleotides shown in Table 10 were prepared in order to insert oligonucleotide 4 into a vector.

TABLE 10

| Intended use | Name | Base Sequence (5'→3') | SEQ ID NO |
|---|---|---|---|
| Insertion into vector | ON4-Sense | GATCCATTTG TCCCCATTAT ATAGCATTTT TTG | 16 |
| | ON4-Antisense | AATTCAAAAA ATGCTATATA ATGGGGACAA ATG | 17 |

The above-described two oligonucleotides ON4-Sense and ON4-Antisense were mixed together at 50 μM each, and annealing (95° C. for 30 seconds, and then 72° C. for 2 minutes, and then 37° C. for 2 minutes, and then 25° C. for 2 minutes) was performed to prepare a double-stranded DNA. The double-stranded DNA was stored at −20° C. until the double-stranded DNA was used in subsequent experiments.

The double-stranded DNA was mixed with an RNAi-Ready pSIREN-RetroQ-ZsGreen vector (manufactured by Takara Bio Inc.), and a ligation reaction was carried out using a Ligation kit (manufactured by Takara Bio Inc.). In the same manner, a control DNA associated with the kit was ligated with an RNAi-Ready pSIREN-RetroQ-ZsGreen vector, and the resultant ligation product was used as a vector for a negative control.

PCR was performed using the primers shown in Table 11, and the formation of a circular plasmid (plasmid vector) by ligation of the above vector and the double-stranded DNA was confirmed.

TABLE 11

| Intended use | Name | Base Sequence (5'→3') | SEQ ID NO |
|---|---|---|---|
| PCR primer | ON4-Fw | ATGGACTATC ATATGCTTAC CGTA | 18 |
| | ON4-Rv | TAATGACCCC GTAATTGATT | 19 |

The plasmid vector obtained above was mixed with HIT competent cells HIT-DH5a (manufactured by RBC Bioscience) and held at 4° C. for 5 minutes. Subsequently, the cells were inoculated onto agar medium and cultured at 37° C. for 18 hours.

The *E. coli* colonies that developed on the agar medium were collected, and PCR was performed using the primers shown in Table 11, as a result of which the introduction of the plasmid vector into *E. coli* was confirmed.

The *E. coli* into which the plasmid vector had been introduced was inoculated in liquid medium and cultured at 37° C. for 16 hours. Thereafter, the plasmid vector was extracted using an ENDOFREE plasmid purification kit (manufactured by QIAGEN). PCR was performed using the primers shown in Table 11, and it was confirmed that the desired plasmid vector was extracted.

A Platinum-GP retroviral packaging cell line (manufactured by Cell Biolabs) was transfected with the above-described plasmid vector and a pCMV-VSV-G envelope vector (manufactured by Cell Biolabs) using a FUGENE HD transfection reagent (manufactured by Roche), thereby producing a retrovirus vector. A culture supernatant containing the retrovirus vector was collected and filtrated, and thereafter stored at −20° C.

Preparation of Oligonucleotide 4-Expressing Raji Cells

Raji cells were cultured in a medium containing the above-described culture supernatant for 48 hours, to infect the Raji cells with the retrovirus vector, thereby preparing Raji cells constitutively expressing oligonucleotide 4 (which were labelled with a fluorescent protein ZsGreen).

Subsequently, ZsGreen positive cells were sorted by FACS.

Measurement of GRα and GRβ Expression Levels

In the same manner as in "Measurement of GRα and GRβ Expression levels" in Example 1, the expressions levels of GRα and GRβ in the oligonucleotide 4-expressing Raji cells were determined. The expression level of GAPDH was determined as an endogenous control.

The expression levels of GAPDH, GRα, and GRβ are shown in Table 12. In Table 12, "relative value of GRα/GRβ" means a relative value, assuming that "the value obtained by dividing the expression level of GRα by the expression level GRβ" in the control Raji cells is 1.

Each experiment was performed in triplicate. The values noted in Table 12 are average values thereof.

TABLE 12

| Cell type | GAPDH | GRα | GRβ | GRα/GAPDH | GRβ/GAPDH | Relative value of GRα/GRβ |
|---|---|---|---|---|---|---|
| Control Raji cell | 6748.018 | 2309.506 | 4552.624 | 0.342 | 0.675 | 1 |
| Oligonucleotide 4-expressing Raji cell | 6428.135 | 4803.456 | 1866.325 | 0.747 | 0.290 | 5.074 |

As is apparent from Table 12, it is confirmed that constitutive expression of oligonucleotide 4 increases the expression level of GRα but decreases the expression level of GRβ.

Examination of Glucocorticoid Sensitivity

In order to examine the glucocorticoid sensitivity of the oligonucleotide 4-expressin Raji cells, BrdU incorporation assay was performed in the same manner as in Example 2, and cell proliferation was quantified. The concentration of dexamethasone was set to 0 μM (no addition) or 5 μM. The results of absorbance measurements are shown in Table 13. Each experiment was repeated in triplicate. The values shown in Table 13 are average of thereof.

TABLE 13

| | | Cell type | | | |
|---|---|---|---|---|---|
| | | Control Raji cell | | oligonucleotide 4-expressing Raji cell | |
| | | Additive amount [μM] of dexamethasone | | | |
| | | 0 | 5 | 0 | 5 |
| BrdU incorporation | Average | 1.14 | 1.07 | 1.13 | 0.58 |
| | SE | 0.04 | 0.05 | 0.01 | 0.08 |

As is apparent from Table 13, in the oligonucleotide 4-expressing Raji cells, the addition of dexamethasone resulted in a significant reduction in BrdU incorporation, as compared to the control Raji cells. Therefore, it is confirmed that constitutive expression of oligonucleotide 4 increases glucocorticoid sensitivity.

Figure 6:
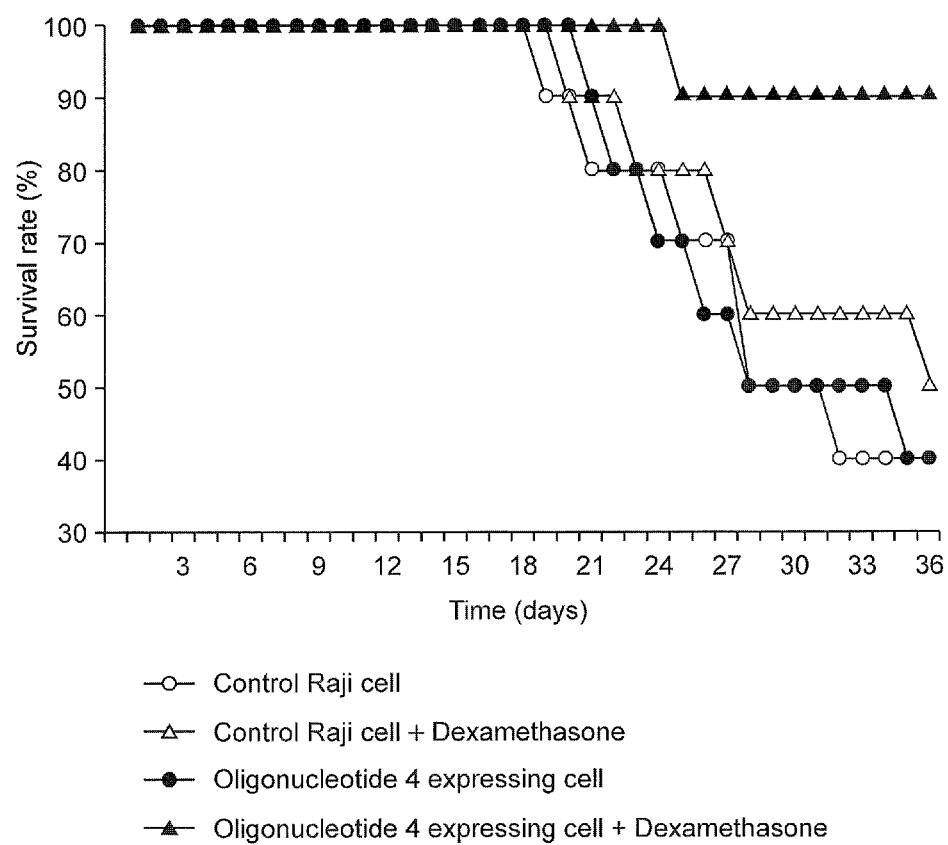
FIG. 6 is a graph showing the cell proliferation inhibitory rate in Example 4.

In Vitro Test 6-week-old SCID mice (n=10) were each inoculated intraperitoneally with 1×10$^7$ cells of the oligonucleotide 4-expressing Raji cells or the control Raji cells, and everyday received intraperitoneal administration of dexamethasone at a dose of 15 mg/kg, during which the mice were observed. The survival rates (%) are shown in Table 14, and the survival curves are shown in FIG. 6.

TABLE 14

| Day | 1 | 2 | 3 | 4 | 5 | 6 | 7 | 8 | 9 | 10 | 11 | 12 |
|---|---|---|---|---|---|---|---|---|---|---|---|---|
| Control Raji cells | 100 | 100 | 100 | 100 | 100 | 100 | 100 | 100 | 100 | 100 | 100 | 100 |
| Control Raji cells + dexamethasone | 100 | 100 | 100 | 100 | 100 | 100 | 100 | 100 | 100 | 100 | 100 | 100 |
| oligonucleotide 4-expressing Raji cells | 100 | 100 | 100 | 100 | 100 | 100 | 100 | 100 | 100 | 100 | 100 | 100 |
| oligonucleotide 4-expressing Raji cells + dexamethasone | 100 | 100 | 100 | 100 | 100 | 100 | 100 | 100 | 100 | 100 | 100 | 100 |

| Day | 13 | 14 | 15 | 16 | 17 | 18 | 19 | 20 | 21 | 22 | 23 | 24 |
|---|---|---|---|---|---|---|---|---|---|---|---|---|
| Control Raji cells | 100 | 100 | 100 | 100 | 100 | 100 | 90 | 90 | 80 | 80 | 80 | 80 |
| Control Raji cells + dexamethasone | 100 | 100 | 100 | 100 | 100 | 100 | 100 | 90 | 90 | 90 | 80 | 80 |
| oligonucleotide 4-expressing Raji cells | 100 | 100 | 100 | 100 | 100 | 100 | 100 | 100 | 90 | 80 | 80 | 70 |
| oligonucleotide 4-expressing Raji cells + dexamethasone | 100 | 100 | 100 | 100 | 100 | 100 | 100 | 100 | 100 | 100 | 100 | 100 |

| Day | 25 | 26 | 27 | 28 | 29 | 30 | 31 | 32 | 33 | 34 | 35 | 36 |
|---|---|---|---|---|---|---|---|---|---|---|---|---|
| Control Raji cells | 70 | 70 | 70 | 50 | 50 | 50 | 50 | 40 | 40 | 40 | 40 | 40 |
| Control Raji cells + dexamethasone | 80 | 80 | 70 | 60 | 60 | 60 | 60 | 60 | 60 | 60 | 60 | 50 |
| oligonucleotide 4-expressing Raji cells | 70 | 60 | 60 | 50 | 50 | 50 | 50 | 50 | 50 | 50 | 40 | 40 |
| oligonucleotide 4-expressing Raji cells + dexamethasone | 90 | 90 | 90 | 90 | 90 | 90 | 90 | 90 | 90 | 90 | 90 | 90 |

As is apparent from Table 14 and FIG. 6, the lethality of the mice inoculated with the oligonucleotide 4-expressing Raji cells was comparable to that of the mice inoculated with the control Raji cells. However, although the administration of dexamethasone to the mice inoculated with the control Raji cells did not increase the survival rate of the mice, the administration of dexamethasone to the mice inoculated with the oligonucleotide 4-expressing Raji cells significantly increased the survival rate of the mice.

Example 5

Examination of Blocking Activity of Oligonucleotide

In order to confirm that oligonucleotide 4 inhibits the binding of SRp30c to a GR pre-mRNA, an RNA-chromatin immunoprecipitation reaction was performed.

RNA-Chromatin Immunoprecipitation Reaction

Oligonucleotide 4-expressing Raji cells and control Raji cells were fixed with 1% formaldehyde to cross-link nucleic acids to proteins.

After the cells were washed, the cells were lysed, treated with a DNase, treated with an RNase inhibitor, and subjected to an immunoprecipitation reaction (at 4° C. for 4 hours) with an anti-SRp30c antibody and protein G magnetic beads ("beads"), using an RNA ChIP-IT kit (manufactured by Active Motif Inc.).

The beads were then recovered and washed, and subjected to treatment for cancelling cross-links.

The GR pre-mRNA that was bound to SRp30c was detected by RT-PCR and PCR using the primers shown in Table 15. The PCR conditions include: performing an initial denaturation at 94° C. for 2 minutes; performing 35 cycles of denaturation (94° C. for 30 seconds), annealing (55° C. for 30 seconds), and extension (72° C. for 1 minute); and then performing a final extension at 72° C. for 4 minutes.

The primers shown in Table 15 were designed to amplify a part of the GR pre-mRNA sequence that corresponds to base numbers 152873 to 153556 of the human GR gene.

TABLE 15

| Intended use | Name | Sequence (5'→3') | SEQ ID NO |
|---|---|---|---|
| PCR primer | Pre-mRNA-Fw | GAGGGAAGGA AACTCCAGCC AGAA | 20 |
| | Pre-mRNA-Rv | TTTCAGCTAA CATCTCGGGG | 21 |

After the PCR was performed, DNA was separated by two-dimensional electrophoresis on a 2% agarose gel containing ethidium bromide, and the intensity of bands was quantified using an image analyzer GEL PRINT 2000i/VGA (manufactured by Genomic Solutions). The relative values assuming that the intensity of the positive control is 1 are shown in Table 16. Each experiment was performed in triplicate. The values noted in Table 16 are average values thereof.

TABLE 16

| | Positive control | Control Raji cell | oligonucleotide 4-expressing Raji cell |
|---|---|---|---|
| Average | 1 | 1.156 | 0.398 |
| SE | 0 | 0.130 | 0.124 |

As is apparent from Table 16, the level of GR pre-mRNA bound to SRp30c was significantly low in the extract from the oligonucleotide 4-expressing Raji cells. Therefore, it is confirmed that the binding of SRp30c to GR pre-mRNA is inhibited in the oligonucleotide 4-expressing Raji cells.

The disclosure of Japanese Patent Application No. 2011-274897, filed Dec. 15, 2011, is incorporated herein by reference in its entirety.

All publications, patent applications, and technical standards mentioned in this specification are herein incorporated by reference to the same extent as if each individual publication, patent application, or technical standard was specifically and individually indicated to be incorporated by reference.

The invention claimed is:

1. A pharmaceutical composition comprising a phosphorothioate oligonucleotide that (i) consists of a nucleotide sequence set forth in SEQ ID NO:1, 2, 3, 4, or 5; or (ii) consists of a nucleotide sequence that has at least 90% sequence identity to SEQ ID NO:1, 2, 3, 4, or 5 and inhibits binding of SRp30c to SEQ ID NO:22.

2. An expression vector comprising a polynucleotide sequence that (i) consists of a nucleotide sequence set forth in SEQ ID NO:1, 2, 3, 4, or 5; or (ii) consists of a nucleotide sequence that has at least 90% sequence identity to SEQ ID NO:1, 2, 3, 4, or 5 and inhibits binding of SRp30c to SEQ ID NO:22.

3. The pharmaceutical composition according to claim 1, wherein the phosphorothioate oligonucleotide consists of a nucleotide sequence that has at least 90% sequence identity to SEQ ID NO:1, 2, 3, 4, or 5 and inhibits binding of SRp30c to SEQ ID NO:22.

4. The expression vector according to claim 2, wherein the polynucleotide sequence consists of a nucleotide sequence that has at least 90% sequence identity to SEQ ID NO:1, 2, 3, 4, or 5 and inhibits binding of SRp30c to SEQ ID NO:22.

5. The pharmaceutical composition according to claim 1, wherein the oligonucleotide is an oligonucleotide having a base sequence represented by SEQ ID NO:1, an oligonucleotide having a base sequence represented by SEQ ID NO:2, an oligonucleotide having a base sequence represented by SEQ ID NO:3, an oligonucleotide having a base sequence represented by SEQ ID NO:4, or an oligonucleotide having a base sequence represented by SEQ ID NO:5.

6. The expression vector according to claim 2, wherein the polynucleotide sequence is a polynucleotide sequence having a base sequence represented by SEQ ID NO:1, a polynucleotide sequence oligonucleotide having a base sequence represented by SEQ ID NO:2, a polynucleotide sequence having a base sequence represented by SEQ ID NO:3, a polynucleotide sequence having a base sequence represented by SEQ ID NO:4, or a polynucleotide sequence having a base sequence represented by SEQ ID NO:5.

7. The pharmaceutical composition according to claim 1, further comprising a solid medium and a liquid medium, wherein the solid medium is selected from the group consisting of gelatin and lactose, and the liquid medium is selected from the group consisting of water, physiological saline, and a glucose aqueous solution.

8. The pharmaceutical composition according to claim 5, further comprising a solid medium and a liquid medium, wherein the solid medium is selected from the group consisting of gelatin and lactose, and the liquid medium is selected from the group consisting of water, physiological saline, and a glucose aqueous solution.

9. A method of enhancing glucocorticoid sensitivity comprising administering to a subject (a) the composition of claim 6; (b) the expression vector of claim 2, or (c) a composition comprising a polynucleotide sequence that (i) consists of a nucleotide sequence set forth in SEQ ID NO:1, 2, 3, 4, or 5; or (ii) consists of a nucleotide sequence that has at least 90% sequence identity to SEQ ID NO:1, 2, 3, 4, or 5 and inhibits binding of SRp30c to SEQ ID NO:22.

10. The method according to claim 9, wherein the polynucleotide sequence is a polynucleotide sequence having a base sequence represented by SEQ ID NO:1, a polynucleotide sequence oligonucleotide having a base sequence represented by SEQ ID NO:2, a polynucleotide sequence having a base sequence represented by SEQ ID NO:3, a polynucleotide sequence having a base sequence represented by SEQ ID NO:4, or a polynucleotide sequence having a base sequence represented by SEQ ID NO:5.

11. A method of treating an allergic disease, an autoimmune disease, a cancer, an endocrine system disease, a psychiatric disorder, an infection, or an injury, the method comprising administering, in combination with glucocorticoid, the pharmaceutical composition according to claim 6 to a subject suffering from an allergic disease, an autoimmune disease, a cancer, an endocrine system disease, a psychiatric disorder, an infection, or an injury.

12. The method according to claim 11, wherein the pharmaceutical composition is administered simultaneously with administration of the glucocorticoid.

13. The method according to claim 11, wherein the pharmaceutical composition is administered before or after administration of the glucocorticoid.

14. The method according to claim 11, wherein the oligonucleotide is an oligonucleotide having a base sequence represented by SEQ ID NO:1, an oligonucleotide having a base sequence represented by SEQ ID NO:2, an oligonucleotide having a base sequence represented by SEQ ID NO:3, an oligonucleotide having a base sequence represented by SEQ ID NO:4, or an oligonucleotide having a base sequence represented by SEQ ID NO:5.

* * * * *